US010690673B2

(12) United States Patent
Lou et al.

(10) Patent No.: US 10,690,673 B2
(45) Date of Patent: Jun. 23, 2020

(54) METHOD OF TREATING CANCER METASTASIS BY CDK 4/6 INHIBITORS

(71) Applicant: Mayo Foundation for Medical Education and Research, Rochester, MN (US)

(72) Inventors: Zhenkun Lou, Rochester, MN (US); Tongzheng Liu, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/089,820

(22) PCT Filed: Mar. 28, 2017

(86) PCT No.: PCT/US2017/024495
§ 371 (c)(1),
(2) Date: Sep. 28, 2018

(87) PCT Pub. No.: WO2017/172734
PCT Pub. Date: Oct. 5, 2017

(65) Prior Publication Data
US 2019/0120844 A1  Apr. 25, 2019

Related U.S. Application Data

(60) Provisional application No. 62/314,807, filed on Mar. 29, 2016.

(51) Int. Cl.
*G01N 33/574* (2006.01)
*A61P 35/04* (2006.01)
(Continued)

(52) U.S. Cl.
CPC ... *G01N 33/57415* (2013.01); *A61K 31/4709* (2013.01); *A61K 31/505* (2013.01);
(Continued)

(58) Field of Classification Search
CPC .............. A61K 31/4709; A61K 31/505; A61K 31/506; A61K 31/519; A61P 35/04; G01N 2333/948; G01N 2800/52; G01N 33/57415
See application file for complete search history.

(56) References Cited

U.S. PATENT DOCUMENTS

2005/0059670 A1  3/2005 Beylin et al.
2009/0208446 A1  8/2009 Johnston et al.
(Continued)

FOREIGN PATENT DOCUMENTS

WO  WO 2015/059044  4/2015
WO  WO 2015/069266  5/2015

OTHER PUBLICATIONS

Mayer (Curr. Oncol. Rep (2015) 17:20 pp. 1-5) (Year: 2015).*
(Continued)

*Primary Examiner* — Savitha M Rao
(74) *Attorney, Agent, or Firm* — Fish & Richardson P.C.

(57) ABSTRACT

This document provides materials and methods for treating cancer metastases. For example, materials and methods for using a CDK 4/6 inhibitor and/or a CDK1 inhibitor to prevent cancer cell metastasis, prevent further cancer cell metastasis, reduce the number of metastatic cancer cells, and/or reduce the risk of cancer cell metastasis within a mammal (e.g., a human) are provided.

6 Claims, 24 Drawing Sheets

(51) Int. Cl.
A61K 31/4709 (2006.01)
A61K 31/505 (2006.01)
A61K 31/506 (2006.01)
A61K 31/519 (2006.01)

(52) U.S. Cl.
CPC .......... A61K 31/506 (2013.01); A61K 31/519 (2013.01); A61P 35/04 (2018.01); G01N 2333/948 (2013.01); G01N 2800/52 (2013.01)

(56) References Cited

U.S. PATENT DOCUMENTS

2014/0107114 A1  4/2014  Kim et al.
2014/0227222 A1  8/2014  Sharpless et al.

OTHER PUBLICATIONS

Asghar et al., "The history and future of targeting cyclin-dependent kinases in cancer therapy," Nat. Rev. Drug Discov., 14(2):130-146, 2015.
Bacac, "Metastatic cancer cell," Annu. Rev. Pathol., 3:221-247, Feb. 2008.
Baek, "Cytokine-regulated protein degradation by the ubiquitination system," Curr. Protein Pept. Sci., 7(2):171-177, Apr. 2006.
Batlle et al., "The transcription factor snail is a repressor of E-cadherin gene expression in epithelial tumour cells," Nat. Cell Biol., 2:84-89, Feb. 2000.
Beaver et al., "FDA Approval: Palbociclib for the Treatment of Postmenopausal Patients with Estrogen Receptor-Positive, HER2-Negative Metastatic Breast Cancer," Clin. Cancer Res., 21(21):4760-4766, Nov. 2015.
Burrows et al., "The DUB/USP17 deubiquitinating enzymes, a multigene family within a tandemly repeated sequence," Genomics, 85(4):524-529, Apr. 2005.
Cano et al., "The transcription factor snail controls epithelial-mesenchymal transitions by repressing E-cadherin expressio," Nat. Cell Biol., 2(2):76-83, Feb. 2000.
Chaffer and Weinberg, "A perspective on cancer cell metastasis," Science, 331(6024):1559-1564, Mar. 2011.
Chaffer and Weinberg, "How does multistep tumorigenesis really proceed?" Cancer Discov., 5(1):22-24, Jan. 2015.
Chiang and Massague, "Molecular basis of metastasis," N. Engl. J. Med., 359:2814-2823, Dec. 2008.
Davis et al., "Targeting EMT in cancer: opportunities for pharmacological intervention," Trends Pharmacol. Sci., 35(9):479-488, Sep. 2014.
De Herreros, "Snail family regulation and epithelial mesenchymal transitions in breast cancer progression," J. Mammary Gland Biol. Neoplasia., 15(2):135-147, Jun. 2010.
Delgado-Diaz et al., "Dub3 controls DNA damage signalling by direct deubiquitination of H2AX," Mol. Oncol., 8(5):884-893, Jul. 2014.
Dickson et al., "Phase II trial of the CDK4 inhibitor PD0332991 in patients with advanced CDK4-amplified well-differentiated or dedifferentiated liposarcoma," J. Clin. Oncol., 31(16):2024-2028, Jun. 2013.
Dong et al., "G9a interacts with Snail and is critical for Snail-mediated E-cadherin repression in human breast cancer," J. Clin. Invest., 122(4):1469-1486, Apr. 2012.
Feng et al., "Epithelial-to-mesenchymal transition activates PERK-eIF2alpha and sensitizes cells to endoplasmic reticulum stress," Cancer Discov., 4(6):702-715, Jun. 2014.
Finn et al., "PD 0332991, a selective cyclin D kinase 4/6 inhibitor, preferentially inhibits proliferation of luminal estrogen receptor-positive human breast cancer cell lines in vitro," Breast Cancer Res., 11(5):R77, Oct. 2009.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study," Lancet. Oncol., 16:25-35, Jan. 2015.
Fischer et al., "Epithelial-to-mesenchymal transition is not required for lung metastasis but contributes to chemoresistance," Nature, 527(7579):472-476, Nov. 2015.
Guarino et al., "The role of epithelial-mesenchymal transition in cancer pathology," Pathology 39(3):305-318, Jan. 2007.
Gupta et al., "The evolving portrait of cancer metastasis," Cold Spring Harb. Symp. Quant Biol., 70:291-297, Jan. 2005.
Hay, "An overview of epithelio-mesenchymal transformation," Cells Tissues Organs, 154:8-20, 1995.
Horiuchi et al., "MYC pathway activation in triple-negative breast cancer is synthetic lethal with CDK inhibition," J. Exp. Med., 209(4):679-696, Apr. 2012.
Huang et al., "Phosphorylation-dependent activity of the deubiquitinase DUBA," Nat. Struct. Mol. Biol., 19(2):171-175, Feb. 2012.
International Search Report in International Application No. PCT/US2017/024495 dated Aug. 25, 2017, 4 pages.
Jiang et al., "RB1 and p53 at the crossroad of EMT and triple-negative breast cancer," Cell Cycle, 10(10):1563-1570, May 2011.
Kalluri and Weinberg, "The basics of epithelial-mesenchymal transition," J. Clin. Invest, 119(6):1420-1428, Jun. 2009.
Kang and Massague, "Epithelial-mesenchymal transitions: twist in development and metastasis," Cell, 118:277-279, Aug. 2004.
Lamouille et al., "Molecular mechanisms of epithelial-mesenchymal transition," Nat. Rev. Mol. Cell Biol., 15(3):178-196, Mar. 2014.
Liu et al., "CDK4/6-dependent activation of DUB3 regulates cancer metastasis through SNAIL1," Nat. Commu., 8:13923, Jan. 2017.
Lopez-Otin and Hunter, "The regulatory crosstalk between kinases and proteases in cancer," Nat. Rev. Cancer, 10:278-292, Apr. 2010.
MacPherson et al., "Phosphorylation of serine 11 and serine 92 as new positive regulators of human Snail 1 function: potential involvement of casein kinase-2 and the cAMP-activated kinase protein kinase a," Mol. Biol. Cell, 21(2):244-253, Jan. 2010.
McFarlane et al., "The deubiquitinating enzyme USP17 is highly expressed in tumor biopsies, is cell cycle regulated, and is required for G1-S progression," Cancer Research, 70(8):3329-39, Apr. 2010.
Peinado et al., "Snail mediates E-cadherin repression by the recruitment of the Sin3A/histone deacetylase 1 (HDAC1)/HDAC2 complex," Mol. Cell Biol., 24:306-319, Jan. 2004.
Peinado et al., "Snail, Zeb and bHLH factors in tumour progression: an alliance against the epithelial phenotype?" Nat. Rev. Cancer, 7(6):415-428, Jun. 2007.
Pereg et al., "Ubiquitin hydrolase Dub3 promotes oncogenic transformation by stabilizing Cdc25A," Nat. Cell Biol., 12(4):400-406, Apr. 2010.
Polyak and Weinberg, "Transitions between epithelial and mesenchymal states: acquisition of malignant and stem cell traits," Nat. Rev. Cancer, 9(4):265-273, Apr. 2009.
Rivadeneira et al., "Proliferative suppression by CDK4/6 inhibition: complex function of the retinoblastoma pathway in liver tissue and hepatoma cells," Gastroenterology, 138(5):1920-1930, May 2010.
Rokavec et al., "IL-6R/STAT3/miR-34a feedback loop promotes EMT-mediated colorectal cancer invasion and metastasis," J. Clin. Invest, 124(4):1853-1867, Apr. 2014.
Shen and Huang, "The role of Cdc25A in the regulation of cell proliferation and apoptosis," Anticancer Agents Med. Chem., 12(6):631-639, Jul. 2012.
Sherr et al., "Targeting CDK4 and CDK6: From Discovery to Therapy," Cancer Discov., 6(4):353-67, Apr. 2016.
Stefansson et al., "CpG island hypermethylation of BRCA1 and loss of pRb as co-occurring events in basal/triple-negative breast cancer," Epigenetics, 6(5):638-649, May 2011.
Sullivan et al., "Interleukin-6 induces an epithelial-mesenchymal transition phenotype in human breast cancer cells," Oncogene, 28(33):2940-2947, Aug. 2009.
Sun et al., "Activation of the ATM-Snail pathway promotes breast cancer metastasis," J. Mol. Cell Biol., 4(5):304-315, Aug. 2012.
Takeichi, "Cadherin cell adhesion receptors as a morphogenetic regulator," Science, 251:1451-1455, 1991.
Tam and Weinberg, "The epigenetics of epithelial-mesenchymal plasticity in cancer," Nat. Med., 19(11):1438-1449, Nov. 2013.

(56) References Cited

OTHER PUBLICATIONS

Thiery et al., "Epithelial-mesenchymal transitions in development and disease," Cell, 139(5):871-890, Nov. 2009.
Thiery, "Epithelial-mesenchymal transitions in tumour progression," Nat. Rev. Cancer, 2(6):442-454, Jun. 2002.
Tsai and Yang, "Epithelial-mesenchymal plasticity in carcinoma metastasis," Genes Dev., 27(20):2192-2206, Oct. 2013.
Tse and Kalluri, "Mechanisms of metastasis: epithelial-to-mesenchymal transition and contribution of tumor microenvironment," J. Cell Biochem., 101(4):816-829, Jul. 2007.
Turley et al., "Mechanisms of disease: epithelial-mesenchymal transition—does cellular plasticity fuel neoplastic progression," Nat. Clin. Pract. Oncol., 5(5):280-290, May 2008.
Valastyan and Weinberg, "Tumor metastasis: molecular insights and evolving paradigms," Cell, 147(2):275-292, Oct. 2011.
Van der Laan et al., "High Dub3 expression in mouse ESCs couples the G1/S checkpoint to pluripotency," Mol. Cell, 52(3):366-379, Nov. 2013.
Vega et al., "Snail blocks the cell cycle and confers resistance to cell death," Genes Dev., 18(10):1131-1143, May 2004.
Vernon and LaBonne, "Tumor metastasis: a new twist on epithelial-mesenchymal transitions," Curr. Biol., 14(17):R719-721, Sep. 2004.
Vinas-Castells et al., "The hypoxia-controlled FBXL14 ubiquitin ligase targets SNAIL1 for proteasome degradation," J. Biol. Chem., 285(6):3794-3805, Feb. 2010.
Wu et al., "Stabilization of snail by NF-kappaB is required for inflammation-induced cell migration and invasion," Cancer Cell, 15(5):416-428, May 2009.

Yang and Weinberg, "Epithelial-mesenchymal transition: at the crossroads of development and tumor metastasis," Dev. Cell, 14:818-829, 2008.
Ye and Weinberg, "Epithelial-Mesenchymal Plasticity: A Central Regulator of Cancer Progression," Trends Cell Biol., 25(11):675-686, Nov. 2015.
Zhang et al., "The collagen receptor discoidin domain receptor 2 stabilizes SNAIL1 to facilitate breast cancer metastasis," Nat. Cell Biol., 15(6):677-687, Jun. 2013.
Zheng et al., "Epithelial-to-mesenchymal transition is dispensable for metastasis but induces chemoresistance in pancreatic cancer," Nature, 527(7579):525-530, Nov. 2015.
Zheng et al., "PKD1 phosphorylation-dependent degradation of SNAIL by SCF-FBXO11 regulates epithelial-mesenchymal transition and metastasis," Cancer Cell, 26(3):358-373, Sep. 2014.
Zhou et al., "Dual regulation of Snail by GSK-3beta-mediated phosphorylation in control of epithelial-mesenchymal transition," Nat. Cell Biol., 6:931-940, Oct. 2004.
Zhou et al., "Dub3 expression correlates with tumor progression and poor prognosis in human epithelial ovarian cancer," Biomedicine & Pharmacotherapy, 70:84-89, Mar. 2015.
Zhou, "Determine the Functional Role Dub3 in Breast Cancer Progression and Metastasis," University of Kentucky, Lexington, KY, United States, 2015 [retrieved on Mar. 15, 2016]. Retrieved from the Internet: <URL: http://grantome.com/grant/NIH/R01-CA188118-01A1>, 3 pages.

* cited by examiner

A

| SNAIL1 | |
|---|---|
| Protein | Number of Peptides |
| DUB3 | 28 |
| SNAIL1 | 25 |
| ATM | 14 |
| USP10 | 8 |
| USP7 | 7 |
| p53 | 5 |
| p38 | 5 |
| USP11 | 4 |
| DNMT1 | 3 |
| CSNK2A1 | 3 |

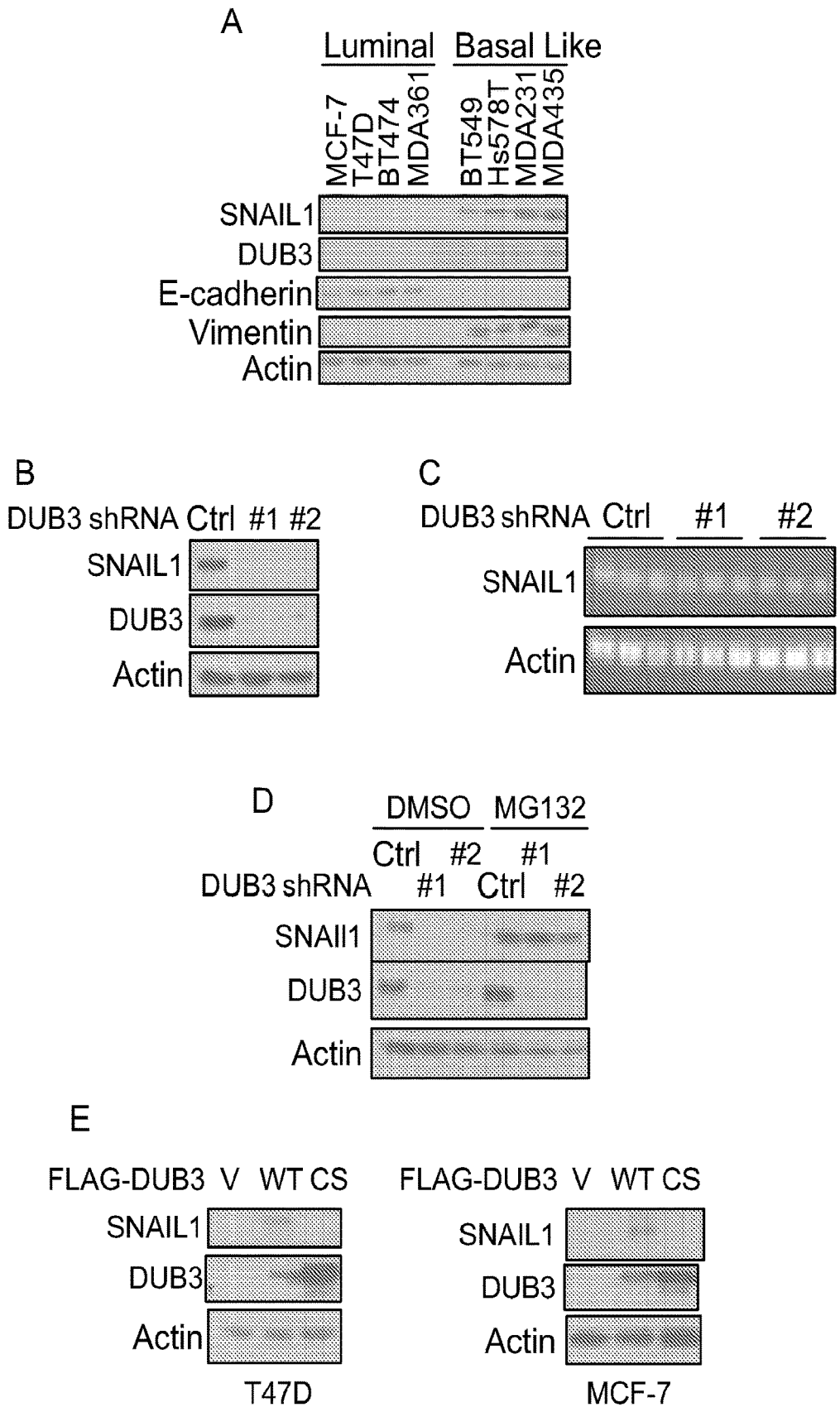

D

E

F

G

H

I

A mDUB3 shRNA Ctrl #6 #10

SNAIL1

DUB3

Actin

B mDUB3 shRNA    Ctrl    #6    #10

|  | SNAIL-Low | SNAIL-High | Total |
|---|---|---|---|
| Non-metastatic Carcinoma | 25 | 25 | 50 |
| Metastatic Carcinoma | 7 | 43 | 50 |
| Total | 23 | 68 | 100 |

$P = 1 \times 10^{-4}$, $R = 0.386$

D

Metastatic Carcinoma

|  | SNAIL-Low | SNAIL-High | Total |
|---|---|---|---|
| DUB3-low | 6 | 7 | 13 |
| DUB3-high | 1 | 36 | 37 |
| Total | 7 | 43 | 50 |

$P = 1 \times 10^{-4}$, $R = 0.549$

E

Non-metastatic Carcinoma

|  | SNAIL-Low | SNAIL-High | Total |
|---|---|---|---|
| DUB3-low | 16 | 15 | 31 |
| DUB3-high | 9 | 10 | 19 |
| Total | 25 | 25 | 50 |

$P = 0.776$, $R = 0.041$

A

| ScanF | Ascore Seq_A | Ascore 1A | Site 1A | Ascore 2A | Site 2A |
|---|---|---|---|---|---|
| 13012 | LT#SSRPDAAFAEIQR | 17.5 | 21 | 0 | 0 |
| 8875 | T#SLPEKS#PLSSEAR | 0 | 35 | 14.5 | 41 |
| 18864 | LTSSRPDAAFAEIQRTS#LPEKSPLSSEAR | 0 | 36 | 0 | 0 |
| 18196 | LTSSRPDAAFAEIQRTS#LPEKS#PLSSEAR | 5.9 | 36 | 21.1 | 41 |
| 8007 | TSLPEKS#PLSSEAR | 23.3 | 41 | 0 | 0 |
| 7784 | TSLPEKS#PLSSEAR | 26.8 | 41 | 0 | 0 |
| 7891 | TSLPEKS#PLSSEAR | 45.6 | 41 | 0 | 0 |
| 9202 | TSLPEKSPLS#SEAR | 11.6 | 44 | 0 | 0 |
| 18877 | LTSSRPDAAFAEIQRT#SLPEKSPLSSEAR | 7 | 35 | 0 | 0 |
| 10005 | NHHPEQQSSLLNLSS#TTR | 0 | 491 | 0 | 0 |
| 10038 | NHHPEQQSSLLNLS#STTR | 8.7 | 490 | 0 | 0 |

B

C

D

E

A

Sequence

TSLPEKS#PLSSEAR

Predicted Fragmentation Pattern

| Seq | # | b: Δ Error | b | y | y: Δ Error | +1 |
|---|---|---|---|---|---|---|
| T | 1 | --- | 102.055 | --- | --- | 14 |
| S | 2 | --- | 189.087 | 1480.704 | --- | 13 |
| L | 3 | --- | 302.171 | 1393.672 | --- | 12 |
| P | 4 | --- | 399.224 | 1280.588 | 246.663 | 11 |
| E | 5 | 508.601 | 528.266 | 1183.535 | -754.678 | 10 |
| K | 6 | 256.528 | 656.361 | 1054.493 | 227.009 | 9 |
| S# | 7 | 154.629 | 823.360 | 926.398 | 272.078 | 8 |
| P | 8 | --- | 920.412 | 759.400 | 249.325 | 7 |
| L | 9 | 260.165 | 1033.497 | 662.347 | 169.744 | 6 |
| S | 10 | 102.051 | 1120.529 | 549.263 | 289.684 | 5 |
| S | 11 | --- | 1207.561 | 462.231 | 480.202 | 4 |
| E | 12 | 141.864 | 1336.603 | 375.199 | 465.871 | 3 |
| A | 13 | 137.044 | 1407.640 | 246.156 | 487.426 | 2 |
| R | 14 | --- | --- | 175.119 | --- | 1 |

METHOD OF TREATING CANCER METASTASIS BY CDK 4/6 INHIBITORS

CROSS-REFERENCE TO RELATED APPLICATIONS

This application is a National Stage application under 35 U.S.C. § 371 of International Application No. PCT/US2017/024495, having an International Filing Date of Mar. 28, 2017, which claims priority to U.S. Application Ser. No. 62/314,807, filed on Mar. 29, 2016. The disclosure of the prior applications are considered part of the disclosure of this application, and are incorporated in their entirety into this application.

BACKGROUND

1. Technical Field

This document relates to materials and methods for treating cancer metastasis. For example, this document provides methods and materials for identifying a subject as having cancer cells (e.g., triple negative breast cancer cells) and administering an agent that inhibits DUB3 activity (e.g., a CDK 4/6 inhibitor and/or a CDK1 inhibitor) in a manner that prevents cancer cell metastasis, prevents further cancer cell metastasis, reduces the number of metastatic cancer cells, and/or reduces the risk of cancer cell metastasis within a mammal.

2. Background Information

Tumor metastasis, the spread of cancer cells from the original tumor site followed by growth of secondary tumors at distant organs, is the primary cause of cancer deaths and remains poorly understood. Epithelial-mesenchymal transition (EMT) plays a role in enhancing invasiveness and promoting metastasis. EMT is a highly-conserved cellular program in which polarized, immobile epithelial cells are converted to migratory mesenchymal cells. Studies have demonstrated the importance of EMT in tissue regeneration, tumor progression and metastasis (Thiery, *Nat. Rev. Cancer* 2:442-454 (2002); Thiery et al., *Cell* 139:871-890 (2009); Turley et al., *Nat. Clin. Pract. Oncol.* 5:280-290 (2008); and Yang and Weinberg, *Dev. Cell* 14:818-829 (2008)).

SUMMARY

This document provides materials and methods for treating cancer metastasis. In some cases, the materials and methods provided herein can be used to prevent cancer cell metastasis, prevent further cancer cell metastasis, reduce the number of metastatic cancer cells, and/or reduce the risk of cancer cell metastasis within a mammal (e.g., a human). For example, a mammal can be identified as having triple-negative breast cancer cells and/or cancer cells that express a DUB3 polypeptide and/or a SNAIL polypeptide, and a CDK 4/6 inhibitor and/or a CDK1 inhibitor can be administered under conditions wherein the cancer cells do not metastasize and/or do not metastasize further. In some cases, a CDK 4/6 inhibitor and/or a CDK1 inhibitor can be administered under conditions wherein the number of metastatic cancer cells and/or the risk of cancer cell metastasis within a mammal is reduced.

As described herein, a mammal having metastatic cancer cells can be identified as being responsive to treatment with one or more CDK 4/6 inhibitors and/or one or more CDK1 inhibitors to prevent further cancer cell metastasis and/or to reduce the number of metastatic cancer cells within the mammal. For example, cancer cells obtained from a mammal having cancer can be assessed to determine if they express an elevated level of a DUB3 polypeptide and/or an elevated level of a SNAIL polypeptide. If the cancer cells express an elevated level of a DUB3 polypeptide or an elevated level of a SNAIL polypeptide, then the mammal can be classified as having a cancer responsive to treatment with one or more CDK 4/6 inhibitors and/or one or more CDK1 inhibitors to prevent further cancer cell metastasis and/or to reduce the number of metastatic cancer cells within the mammal. If the cancer cells do not express an elevated level of a DUB3 polypeptide or an elevated level of a SNAIL polypeptide, then the mammal can be classified as having a cancer that is not responsive to treatment with one or more CDK 4/6 inhibitors and/or one or more CDK1 inhibitors to prevent further cancer cell metastasis and/or to reduce the number of metastatic cancer cells within the mammal.

In some cases, a mammal having cancer cells (e.g., triple negative breast cancer cells) can be identified as being responsive to treatment with one or more CDK 4/6 inhibitors and/or one or more CDK1 inhibitors to prevent cancer cell metastasis and/or to reduce the risk of cancer cell metastasis within the mammal. For example, cancer cells obtained from a mammal having cancer can be assessed to determine if they express an elevated level of a DUB3 polypeptide and/or an elevated level of a SNAIL polypeptide. If the cancer cells express an elevated level of a DUB3 polypeptide or an elevated level of a SNAIL polypeptide, then the mammal can be classified as having a cancer responsive to treatment with one or more CDK 4/6 inhibitors and/or one or more CDK1 inhibitors to prevent cancer cell metastasis and/or to reduce the risk of cancer cell metastasis within the mammal. If the cancer cells do not express an elevated level of a DUB3 polypeptide or an elevated level of a SNAIL polypeptide, then the mammal can be classified as having a cancer that is not responsive to treatment with one or more CDK 4/6 inhibitors and/or one or more CDK1 inhibitors to prevent cancer cell metastasis and/or to reduce the risk of cancer cell metastasis within the mammal.

In some cases, a mammal identified as having metastatic cancer cells can be effectively treated with one or more CDK 4/6 inhibitors and/or one or more CDK1 inhibitors to prevent further cancer cell metastasis and/or to reduce the number of metastatic cancer cells within the mammal. For example, cancer cells obtained from a mammal having cancer can be assessed to determine if they express an elevated level of a DUB3 polypeptide and/or an elevated level of a SNAIL polypeptide. If the cancer cells express an elevated level of a DUB3 polypeptide or an elevated level of a SNAIL polypeptide, then the mammal can be administered one or more CDK 4/6 inhibitors and/or one or more CDK1 inhibitors to prevent further cancer cell metastasis and/or to reduce the number of metastatic cancer cells within the mammal.

In some cases, a mammal identified as having cancer cells (e.g., triple negative breast cancer cells) can be effectively treated with one or more CDK 4/6 inhibitors and/or one or more CDK1 inhibitors to prevent cancer cell metastasis and/or to reduce the risk of cancer cell metastasis within the mammal. For example, cancer cells obtained from a mammal having cancer can be assessed to determine if they express an elevated level of a DUB3 polypeptide and/or an elevated level of a SNAIL polypeptide. If the cancer cells express an elevated level of a DUB3 polypeptide or an elevated level of a SNAIL polypeptide, then the mammal can be administered one or more CDK 4/6 inhibitors and/or one or more CDK1 inhibitors to prevent cancer cell metastasis and/or to reduce the risk of cancer cell metastasis within the mammal.

In general, one aspect of this document features a method for treating cancer in a mammal. The method comprises, or consists essentially of, (a) identifying the mammal as having triple-negative breast cancer cells, and (b) administering a CDK 4/6 inhibitor to the mammal under conditions wherein the triple-negative breast cancer cells do not metastasize. The mammal can be a human. The CDK 4/6 inhibitor can be selected from the group consisting of PD0332991, LY2835219, and LEE011.

In another aspect, this document features a method for treating cancer in a mammal. The method comprises, or consists essentially of, (a) identifying the mammal as having cancer cells that express an elevated level of a DUB3 polypeptide or an elevated level of a SNAIL polypeptide, and (b) administering a CDK 4/6 inhibitor to the mammal under conditions wherein the cancer cells do not metastasize. The mammal can be a human. The cancer can be a lung cancer, a breast cancer, or an ovarian cancer. The cancer can be a triple negative breast cancer. The DUB3 polypeptide can be phosphorylated at Ser41. The CDK 4/6 inhibitor can inhibit phosphorylation of Ser41 of the DUB3 polypeptide. The CDK 4/6 inhibitor can be selected from the group consisting of PD0332991, LY2835219, and LEE011.

In another aspect, this document features a method for treating cancer in a mammal. The method comprises, or consists essentially of, (a) identifying the mammal as having a triple-negative breast cancer cell metastasis, and (b) administering a CDK 4/6 inhibitor to the mammal under conditions wherein the number of cancer cells of the metastasis within the mammal is reduced. The mammal can be a human. The CDK 4/6 inhibitor can be selected from the group consisting of PD0332991, LY2835219, and LEE011.

In another aspect, this document features a method for treating cancer in a mammal. The method comprises, or consists essentially of, (a) identifying the mammal as having metastatic cancer cells that express an elevated level of a DUB3 polypeptide or an elevated level of a SNAIL polypeptide, and (b) administering a CDK 4/6 inhibitor to the mammal under conditions wherein the number of the metastatic cancer cells within the mammal is reduced. The mammal can be a human. The cancer cells can be lung cancer cells, breast cancer cells, or ovarian cancer cells. The cancer cells can be triple negative breast cancer cells. The method can comprise identifying the mammal as having metastatic cancer cells that express the elevated level of a DUB3 polypeptide. The DUB3 polypeptide can be phosphorylated at Ser41. The CDK 4/6 inhibitor can inhibit phosphorylation of Ser41 of the DUB3 polypeptide. The CDK 4/6 inhibitor can be selected from the group consisting of PD0332991, LY2835219, and LEE011.

In another aspect, this document features a method for identifying a mammal as having triple negative breast cancer susceptible to treatment with a CDK 4/6 inhibitor. The method comprises, or consists essentially of, (a) detecting that the mammal has cancer cells that express an elevated level of a DUB3 polypeptide or an elevated level of a SNAIL polypeptide, and (b) classifying the mammal as having triple negative breast cancer susceptible to treatment with the CDK 4/6 inhibitor. The mammal can be a human. The CDK 4/6 inhibitor can be selected from the group consisting of PD0332991, LY2835219, and LEE011.

In another aspect, this document features a method for identifying a mammal as having a cancer metastasis susceptible to treatment with a CDK 4/6 inhibitor. The method comprises, or consists essentially of, (a) detecting that the mammal has metastatic cancer cells that express an elevated level of a DUB3 polypeptide or an elevated level of a SNAIL polypeptide, and (b) classifying the mammal as a cancer metastasis susceptible to treatment with the CDK 4/6 inhibitor. The mammal can be a human. The cancer metastasis can be a lung cancer metastasis, a breast cancer metastasis, or an ovarian cancer metastasis. The cancer metastasis can be a triple negative breast cancer metastasis. The CDK 4/6 inhibitor can be selected from the group consisting of PD0332991, LY2835219, and LEE011.

In another aspect, this document features a method for treating cancer in a mammal. The method comprises, or consists essentially of, (a) identifying the mammal as having triple-negative breast cancer cells, and (b) administering a CDK1 inhibitor to the mammal under conditions wherein the triple-negative breast cancer cells do not metastasize. The mammal can be a human. The CDK1 inhibitor can be selected from the group consisting of SCH 727965, NU6027 and RO-3306.

In another aspect, this document features a method for treating cancer in a mammal. The method comprises, or consists essentially of, (a) identifying the mammal as having cancer cells that express an elevated level of a DUB3 polypeptide or an elevated level of a SNAIL polypeptide, and (b) administering a CDK1 inhibitor to the mammal under conditions wherein the cancer cells do not metastasize. The mammal can be a human. The cancer can be a lung cancer, a breast cancer, or an ovarian cancer. The cancer can be a triple negative breast cancer. The DUB3 polypeptide can be phosphorylated at Ser41. The CDK1 inhibitor can inhibit phosphorylation of Ser41 of the DUB3 polypeptide. The CDK1 inhibitor can be selected from the group consisting of SCH 727965, NU6027 and RO-3306.

In another aspect, this document features a method for treating cancer in a mammal. The method comprises, or consists essentially of, (a) identifying the mammal as having a triple-negative breast cancer cell metastasis, and (b) administering a CDK1 inhibitor to the mammal under conditions wherein the number of cancer cells of the metastasis within the mammal is reduced. The mammal can be a human. The CDK1 inhibitor can be selected from the group consisting of SCH 727965, NU6027 and RO-3306.

In another aspect, this document features a method for treating cancer in a mammal. The method comprises, or consists essentially of, (a) identifying the mammal as having metastatic cancer cells that express an elevated level of a DUB3 polypeptide or an elevated level of a SNAIL polypeptide, and (b) administering a CDK1 inhibitor to the mammal under conditions wherein the number of the metastatic cancer cells within the mammal is reduced. The mammal can be a human. The cancer cells can be lung cancer cells, breast cancer cells, or ovarian cancer cells. The cancer cells can be triple negative breast cancer cells. The method can comprise identifying the mammal as having metastatic cancer cells that express the elevated level of a DUB3 polypeptide. The DUB3 polypeptide can be phosphorylated at Ser41. The CDK1 inhibitor can inhibit phosphorylation of Ser41 of the DUB3 polypeptide. The CDK1 inhibitor can be selected from the group consisting of SCH 727965, NU6027 and RO-3306.

In another aspect, this document features a method for identifying a mammal as having triple negative breast cancer susceptible to treatment with a CDK1 inhibitor. The method comprises, or consists essentially of, (a) detecting that the mammal has cancer cells that express an elevated level of a DUB3 polypeptide or an elevated level of a SNAIL polypeptide, and (b) classifying the mammal as having triple negative breast cancer susceptible to treatment with the CDK1 inhibitor. The mammal can be a human. The CDK1 inhibitor can be selected from the group consisting of SCH 727965, NU6027 and RO-3306.

In another aspect, this document features a method for identifying a mammal as having a cancer metastasis susceptible to treatment with a CDK1 inhibitor. The method comprises, or consists essentially of, (a) detecting that the mammal has metastatic cancer cells that express an elevated level of a DUB3 polypeptide or an elevated level of a SNAIL polypeptide, and (b) classifying the mammal as a cancer metastasis susceptible to treatment with the CDK1 inhibitor. The mammal can be a human. The cancer metastasis can be a lung cancer metastasis, a breast cancer metastasis, or an ovarian cancer metastasis. The cancer metastasis can be a triple negative breast cancer metastasis. The CDK1 inhibitor can be selected from the group consisting of SCH 727965, NU6027 and RO-3306.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 14. CDK4/6 inhibitor LY2835219 decreases SNAIL1 polypeptide level and inhibits the migratory activity of TNBC cells. (A) MDA-MB-231 cells were treated with vehicle or LY2835219 at the indicated concentration for 24 hours and SNAIL1 polypeptide levels were detected by Western blotting. (B) MDA-MB-231 cells were treated with vehicle or LY2835219 and the migration ability of cells was measured by a wound healing assay. (C) HCC1806, BT549 and MDA-MB-468 cells were treated with vehicle or LY2835219 at the indicated concentration for 24 hours and SNAIL1 polypeptide levels were detected by Western blotting. (D) HCC1806 cells were treated with vehicle or LY2835219 and the migration ability of cells was measured by a wound healing assay.

DETAILED DESCRIPTION

Figure 1:
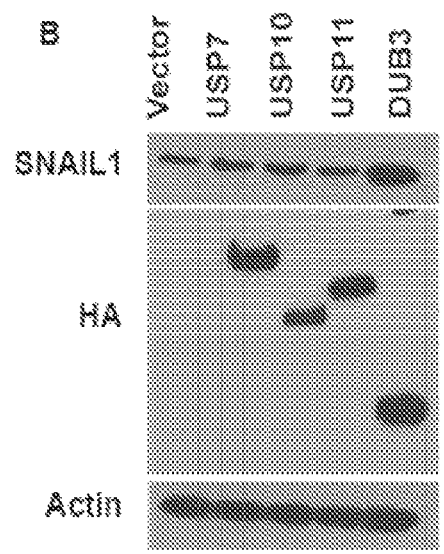
FIG. 1. DUB3 interacts with SNAIL1. (A) List of SNAIL1-associated polypeptides identified by mass spectrometric analysis. MDA-MB-231 cells stably expressing FLAG-SNAIL1 were generated and SNAIL1 complexes were subjected to mass spectrometric analysis. (B) MDA-MB-231 cells were transfected with indicated plasmids and western blotting was performed. (C-D) MDA-MB-231 cell lysates were subjected to immunoprecipitation with control IgG, anti-SNAIL1 (C), or anti-DUB3 (D) antibodies. The immunoprecipitates were then blotted with the indicated antibodies. (E) Purified recombinant GST, GST-DUB3 and His-SNAIL1 were incubated in vitro as indicated. The interaction between DUB3 and SNAIL1 was then examined.
Figure 1:
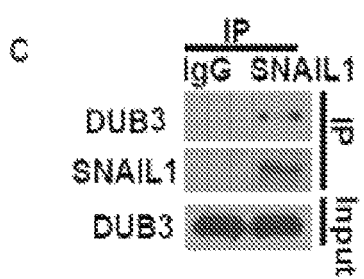
Figure 1:
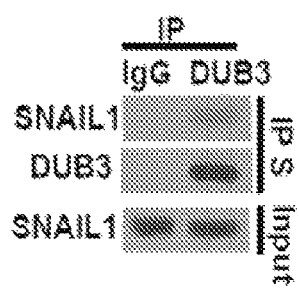
Figure 1:
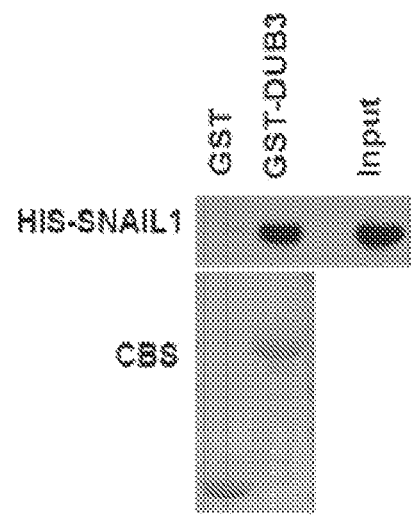
Figure 2:
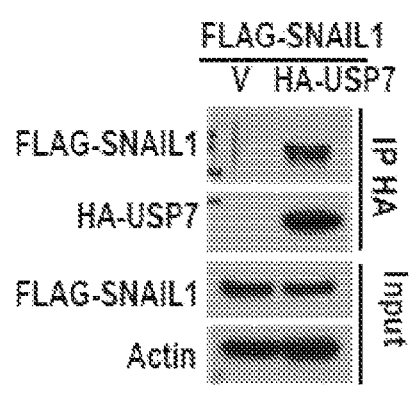
FIG. 2. DUBs interacts with SNAIL1. MDA-MB-231 cells stably expressing FLAG-SNAIL1 were stably transfected with HA-USP7 (A), HA-USP10 (B), HA-USP11 (C) and HA-DUB3 (D). Co-immunoprecipitation experiments were performed using an HA antibody to pull down the HA-tagged deubiquitinases. Western blotting was performed with the indicated antibodies.
Figure 2:
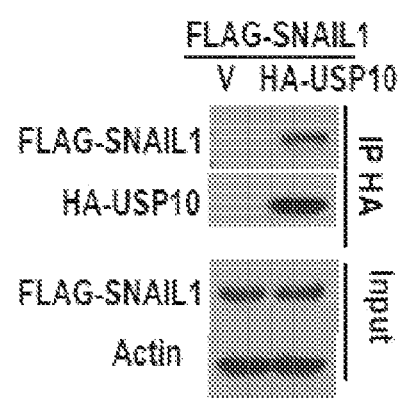
Figure 2:
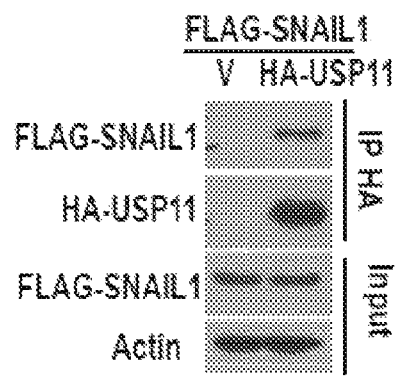
Figure 2:
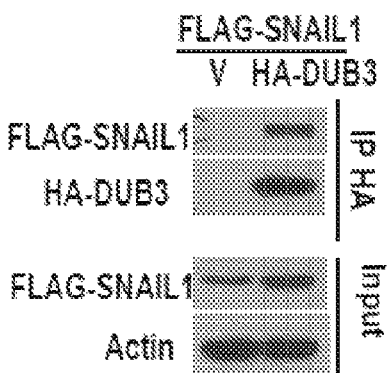

This document provides materials and methods for treating cancer metastasis. In some cases, the materials and methods provided herein can be used to prevent cancer cell metastasis, prevent further cancer cell metastasis, reduce the number of metastatic cancer cells, and/or reduce the risk of cancer cell metastasis within a mammal (e.g., a human).

As described herein, a mammal can be identified as having cancer cells that express an elevated level of a DUB3 polypeptide (and/or an elevated level of a SNAIL polypeptide), and a cyclin-dependent kinase (CDK) 4/6 inhibitor and/or a CDK1 inhibitor can be administered under conditions wherein the cancer cells do not metastasize or do not metastasize further. In some cases, a CDK 4/6 inhibitor and/or a CDK1 inhibitor can be administered under conditions wherein the number of metastatic cancer cells and/or the risk of cancer cell metastasis within a mammal is reduced. In some cases, a CDK 4/6 inhibitor can be administered without administering a CDK1 inhibitor. In some cases, a CDK1 inhibitor can be administered without administering a CDK 4/6 inhibitor. In some cases, a CDK 4/6 inhibitor can be administered in combination with a CDK1 inhibitor (e.g., sequentially or simultaneously).

Any appropriate mammal having cancer can be treated as described herein. For example, humans and other primates such as monkeys having cancer can be identified as having cancer cells that express an elevated level of a DUB3 polypeptide (and/or an elevated level of a SNAIL polypeptide), and treated with one or more CDK 4/6 inhibitors and/or one or more CDK1 inhibitors to prevent cancer cell metastasis, prevent further cancer cell metastasis, reduce the number of metastatic cancer cells, and/or reduce the risk of cancer cell metastasis within the human or other primate. In some cases, dogs, cats, horses, cows, pigs, sheep, mice, and rats can be identified and treated with one or more CDK 4/6 inhibitors and/or one or more CDK1 inhibitors as described herein.

Any appropriate cancer can be assessed for an elevated level of a DUB3 polypeptide (and/or an elevated level of a SNAIL polypeptide). For example, lung cancer, a breast cancer, ovarian cancer, melanoma, pancreatic cancer, or prostate cancer can be assessed an elevated level of a DUB3 polypeptide (and/or an elevated level of a SNAIL polypeptide), and treated with a CDK 4/6 inhibitor and/or a CDK1 inhibitor as described herein.

In some cases, a cancer that can be treated as described herein is a triple-negative breast cancer (TNBC). A TNBC refers to any breast cancer that is estrogen receptor (ER) negative, progesterone receptor (PR) negative, and HER2/neu negative. In some cases, a TNBC can be identified as having an elevated level of a DUB3 polypeptide (and/or an elevated level of a SNAIL polypeptide). Once identified, the TNBC can be treated by administering a CDK 4/6 inhibitor and/or a CDK1 inhibitor.

In some cases, metastasis of cancer cells treated with one or more CDK 4/6 inhibitors and/or one or more CDK1 inhibitors is prevented or prevented from developing further independently of any effect on cancer cell number, cell division, or both. In some cases, the number of metastatic cancer cells following administration of one or more CDK 4/6 inhibitors and/or one or more CDK1 inhibitors is reduced, e.g., by 5%, 10%, 15%, 20%, 25%, 30%, 35%, 40%, 45%, 50%, 55%, 60%, 65%, 70%, 75%, 80%, 85%, 90%, 95%, or more.

Any appropriate method can be used to identify a mammal having cancer. For example, imaging techniques and biopsy techniques can be used to identify mammals (e.g., humans) having cancer.

Once a mammal (e.g., a human) is identified as having cancer, the cancer can be assessed to determine if the cancer cells express an elevated level of a DUB3 polypeptide (and/or an elevated level of a SNAIL polypeptide). Any appropriate method can be used to identify cancer cells having an elevated level of a DUB3 polypeptide (and/or an elevated level of a SNAIL polypeptide). For example, polypeptide-based assays such as Western blot, antibody staining techniques, or ELISAs using anti-DUB3 polypeptide antibodies or anti-SNAIL polypeptide antibodies can be performed to identify cancer cells as having an elevated level of a DUB3 polypeptide or an elevated level of a SNAIL polypeptide. In some case, the cancer can be assessed to determine if the cancer cells express a DUB3 polypeptide that is phosphorylated at Ser41. For example, an antibody specific for phosphorylated Ser41 can be used in an assay (e.g., a Western blot of a cellular lysate) to detect the presence of a DUB3 polypeptide that is phosphorylated at Ser41. In some case, the cancer can be assessed to determine if the cancer cells have an elevated level of a DUB3 polypeptide (and/or an elevated level of a SNAIL polypeptide) by assaying for the level of DUB3 mRNA (and/or SNAIL mRNA). For example, mRNA-based assays such as RT-PCR, Northern blotting, nuclease or protection assays be used to identify cancer cells as having an elevated level of DUB3 mRNA (and/or an elevated level of a SNAIL mRNA), and thus an elevated level of a DUB3 polypeptide (and/or an elevated level of a SNAIL polypeptide).

In some cases, the term "elevated level" as used herein with respect to a level of DUB3 polypeptide (or SNAIL polypeptide) expression by a cancer cell can refer to a level of polypeptide expression by a cancer cell that is greater (e.g., at least 5, 10, 25, 35, 45, 50, 55, 65, 75, 80, 90, or 100 percent greater) than that observed by neighboring non-cancerous cells, for example, within the same tissue sample obtained for the mammal (e.g., human). In some cases, the term "elevated level" as used herein with respect to a level of DUB3 polypeptide (or SNAIL polypeptide) expression by cancer cells can refer to a level of polypeptide expression by cancer cells that is greater (e.g., at least 5, 10, 25, 35, 45, 50, 55, 65, 75, 80, 90, or 100 percent greater) than that observed by comparable cancer cells obtained from the same mammal at an earlier time point (e.g., cancer cells obtained from the same cancer at least 3, 6, 9, 12, or 15 months earlier). In some cases, a mammal can be identified as having cancer cells that express an elevated level of a DUB3 polypeptide (or an elevated level of a SNAIL polypeptide) by assessing polypeptide expression using assays such as immunohistochemical staining or by assessing mRNA expression using assays such as RT-PCR, RNAseq techniques, or microarray techniques.

Once identified as having cancer cells having an elevated level of a DUB3 polypeptide (and/or an elevated level of a SNAIL polypeptide), the mammal can be administered or instructed to self-administer one or more CDK 4/6 inhibitors and/or one or more CDK1 inhibitors to prevent cancer cell metastasis, prevent further cancer cell metastasis, reduce the number of metastatic cancer cells, and/or reduce the risk of cancer cell metastasis within the mammal (e.g., a human). Examples of appropriate CDK 4/6 inhibitors that can be used as described herein include, without limitation, PD0332991 (Palbociclib, Pfizer), LY2835219 (Abemaciclib, Eli Lilly), and LEE011 (Ribociclib, Novartis). In some cases, two or more CDK 4/6 inhibitors (e.g., two, three, four, five, or more CDK 4/6 inhibitors) can be administered to a mammal having cancer cells under conditions wherein such administration prevents cancer cell metastasis, prevents further cancer cell metastasis, reduces the number of metastatic cancer cells, and/or reduces the risk of cancer cell metastasis within the mammal (e.g., a human). Examples of appropriate CDK1 inhibitors that can be used as described herein include, without limitation, SCH 727965, NU6027 and RO-3306. In some cases, two or more CDK1 inhibitors (e.g., two, three, four, five, or more CDK1 inhibitors) can be administered to a mammal having cancer cells under conditions wherein such administration prevents cancer cell metastasis, prevents further cancer cell metastasis, reduces the number of metastatic cancer cells, and/or reduces the risk of cancer cell metastasis within the mammal (e.g., a human).

In some cases, one or more CDK 4/6 inhibitors and/or one or more CDK1 inhibitors can be administered to a mammal once or multiple times over a period of time ranging from days to weeks or to months. In some cases, one or more CDK 4/6 inhibitors and/or one or more CDK1 inhibitors can be formulated into a pharmaceutically acceptable composition for administration to a mammal having cancer. For example, a therapeutically effective amount of a CDK 4/6 inhibitor (e.g., PD0332991, LY2835219, or LEE011) and/or a CDK1 inhibitor (e.g., SCH 727965 or RO-3306 or NU6027) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more CDK 4/6 inhibitors and/or one or more CDK1 inhibitors can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more CDK 4/6 inhibitors and/or one or more CDK1 inhibitors can be administered locally or systemically. For example, a composition provided herein can be administered locally by injection into tumors. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments such as use of other agents, and the judgment of the treating physician.

An effective amount of a composition containing one or more CDK 4/6 inhibitors and/or one or more CDK1 inhibitors can be any amount that prevents cancer cell metastasis, prevents further cancer cell metastasis, reduces the number of metastatic cancer cells, and/or reduces the risk of cancer cell metastasis within the mammal (e.g., a human) without producing significant toxicity to the mammal. For example, an effective amount of a CDK 4/6 inhibitor such as PD0332991, LY2835219, or LEE011 and/or a CDK1 inhibitor such as SCH 727965 or RO-3306 or NU6027 can be from about 1 mg/kg to about 200 mg/kg (e.g., from about 2 mg/kg to about 5 mg/kg, from about 75 mg/kg to about 200 mg/kg, from about 100 mg/kg to about 200 mg/kg, from about 50 mg/kg to about 150 mg/kg, or from about 50 mg/kg to about 100 mg/kg). In some cases, between about 70 mg and about 600 mg of a CDK 4/6 inhibitor and/or a CDK1 inhibitor can be administered to an average sized human (e.g., about 75-85 kg human) daily for about 2 to about 4 weeks. In some cases, a CDK 4/6 inhibitor and a CDK1 inhibitor can be administered in combination, such that the total effective amount of the CDK 4/6 inhibitor and the CDK1 inhibitor combination prevents cancer cell metastasis, prevents further cancer cell metastasis, reduces the number of metastatic cancer cells, and/or reduces the risk of cancer cell metastasis within the mammal (e.g., a human) without producing significant toxicity to the mammal. In some cases, a CDK 4/6 inhibitor and a CDK1 inhibitor can be administered separately, such that the total effective amount of the separately-administered CDK 4/6 inhibitor and the CDK1 inhibitor prevents cancer cell metastasis, prevents further cancer cell metastasis, reduces the number of metastatic cancer cells, and/or reduces the risk of cancer cell metastasis within the mammal (e.g., a human) without producing significant toxicity to the mammal. If a particular mammal fails to respond to a particular amount, then the amount of a CDK 4/6 inhibitor and/or a CDK1 inhibitor can be increased by, for example, two fold. After receiving this higher amount, the mammal can be monitored for both responsiveness to the treatment (e.g., prevention of further cancer cell metastasis and/or reduction in the number of metastatic cancer cells) and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of a CDK 4/6 inhibitor and/or a CDK1 inhibitor can be any amount that prevents cancer cell metastasis, prevents further cancer cell metastasis, reduces the number of metastatic cancer cells, and/or reduces the risk of cancer cell metastasis within the mammal (e.g., a human) without producing significant toxicity to the mammal. For example, the frequency of administration of a CDK 4/6 inhibitor and/or a CDK1 inhibitor can be from about twice daily to about two times a month (e.g., from about once daily to about three times a month). The frequency of administration of a CDK 4/6 inhibitor and/or a CDK1 inhibitor can remain constant or can be variable during the duration of treatment. A course of treatment with a composition containing a CDK 4/6 inhibitor and/or a CDK1 inhibitor can include rest periods. For example, a composition containing one or more CDK 4/6 inhibitors and/or one or more CDK1 inhibitors can be administered twice daily over a two week period followed by a two week rest period, and such a regimen can be repeated multiple times. In some cases, a course of treatment can include alternating administration of a first composition containing one or more CDK 4/6 inhibitors and a second composition containing one or more CDK1 inhibitors. In some cases, a course of treatment can include administering a first composition containing one or more CDK 4/6 inhibitors, in which: a) one or more doses of the administered first composition includes one or more CDK1 inhibitors, and b) one or more doses of the administered first composition does not include one or more CDK1 inhibitors, such that every dose of the course of treatment includes the one or more CDK 4/6 inhibitors, but the one or more CDK1 inhibitors are only included in a subset of the doses. In some cases, a course of treatment can include administering a first composition containing one or more CDK1 inhibitors, in which: a) one or more doses of the administered first composition includes one or more CDK 4/6 inhibitors, and b) one or more doses of the administered first composition does not include one or more CDK 4/6 inhibitors, such that every dose of the course of treatment includes the one or more CDK1 inhibitors, but the one or more CDK 4/6 inhibitors are only included in a subset of the doses. As with the effective amount, various factors can influence the actual frequency of administration used for a particular application. For example, the effective amount, duration of treatment, use of multiple treatment agents, route of administration, and severity of the condition (e.g., type and/or stage of cancer) may require an increase or decrease in administration frequency.

An effective duration for administering a composition containing one or more CDK 4/6 inhibitors and/or one or more CDK1 inhibitors can be any duration that prevents cancer cell metastasis, prevents further cancer cell metastasis, reduces the number of metastatic cancer cells, and/or reduces the risk of cancer cell metastasis within the mammal (e.g., a human) without producing significant toxicity to the mammal. In some cases, the effective duration can vary from several days to several weeks or months. In general, the effective duration for treating a cancer in the mammal can range in duration from about one week to about four weeks. Multiple factors can influence the actual effective duration used for a particular treatment. For example, an effective duration can vary with the frequency of administration, effective amount, use of multiple treatment agents, route of administration, and severity of the condition (e.g., type and/or stage of cancer) being treated.

In certain instances, during a course of treatment, metastasis of cancer cells present within a mammal, and/or the severity of one or more symptoms related to the condition being treated (e.g., cancer) can be monitored. Any appropriate method can be used to monitor metastasis of cancer cells present within a mammal. For example, imaging techniques can be used to assess metastasis of cancer cells present within a mammal. In some cases, lymph nodes of the mammal are monitored for any signs of cancer cells, the presence of cancer cells in a lymph node being indicative of metastasis.

In some cases, an inhibitor of DUB3 polypeptide activity or expression can be used together with a CDK 4/6 inhibitor and/or a CDK1 inhibitor, or in place of a CDK 4/6 inhibitor and/or a CDK1 inhibitor, to treat cancer in a mammal (e.g., to prevent cancer cell metastasis, prevent further cancer cell metastasis, reduce the number of metastatic cancer cells, and/or reduce the risk of cancer cell metastasis within the mammal). Examples of inhibitors of DUB3 polypeptide activity or expression include, without limitation, RNA interference agents such as small interfering RNAs (siRNAs), short hairpin RNAs (shRNAs), and microRNAs (miRNAs). Other examples of inhibitors of DUB3 polypeptide activity or expression that can be used together with or in place of a CDK 4/6 inhibitor and/or a CDK1 inhibitor include antibodies that bind and inactivate a DUB3 polypeptide, other polypeptides that bind and inactivate a DUB3 polypeptide, and small molecules that bind and inactivate a DUB3 polypeptide.

In some cases, an inhibitor of SNAIL1 polypeptide activity or expression can be used together with a CDK 4/6 inhibitor and/or a CDK1 inhibitor, or in place of a CDK 4/6 inhibitor and/or a CDK1 inhibitor, to treat cancer in a mammal (e.g., to prevent cancer cell metastasis, prevent further cancer cell metastasis, reduce the number of metastatic cancer cells, and/or reduce the risk of cancer cell metastasis within the mammal). Examples of inhibitors of SNAIL1 polypeptide activity or expression include, without limitation, RNA interference agents such as small interfering RNAs (siRNAs), short hairpin RNAs (shRNAs), and microRNAs (miRNAs). Other examples of inhibitors of SNAIL1 polypeptide activity or expression that can be used together with or in place of a CDK 4/6 inhibitor and/or a CDK1 inhibitor include antibodies that bind and inactivate a SNAIL1 polypeptide, other polypeptides that bind and inactivate a SNAIL1 polypeptide, and small molecules that bind and inactivate a SNAIL1 polypeptide. In some cases, an agent that promotes ubiquitination and facilitates degradation of the SNAIL1 polypeptide can be used to inhibit SNAIL1.

The invention will be further described in the following examples, which do not limit the scope of the invention described in the claims.

EXAMPLES

Example 1—Identification of DUBs for SNAIL1 Polypeptide Turnover Regulation

To identify potential SNAIL1 regulator, MDA-MB-231 cells stably expressing FLAG-SNAIL1 were used to perform tandem affinity purification and mass spectrometry analysis. In addition to known SNAIL1 interacting polypeptides such as ATM, DNMT1 and CSNK2A1, several DUBs including USP7, USP10, USP11 and DUB3 were identified as major SNAIL1-associated polypeptides (FIG. 1A). Although SNAIL1 interacted with several DUBs (FIG. 2A-D), only overexpression of DUB3, but not USP7, USP10 or USP II dramatically increased polypeptide level of SNAIL1 in MDA-MB-231 (FIG. 1B). The endogenous SNAIL1-DUB3 interaction was confirmed by co-immunoprecipitation (Co-IP). As shown in FIG. 1C, SNAIL1 Co-IPed with DUB3. Reciprocal immunoprecipitation with DUB3 antibodies also brought down SNAIL1 (FIG. 1D). Moreover, GST-DUB3 but not GST could interact with recombinant His-SNAIL1 in vitro, indicating a direct interaction between DUB3 and SNAIL1 (FIG. 1E). It was hypothesized that DUB3 might regulate EMT and cancer metastasis through SNAIL 1.

Figure 3:
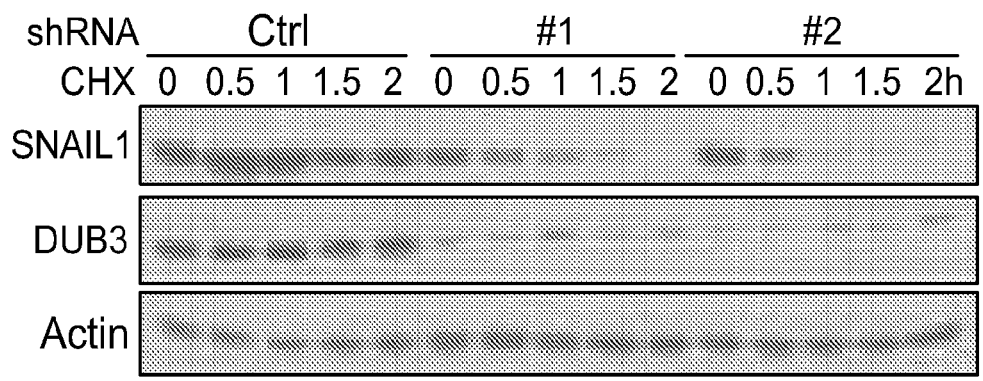
FIG. 3. DUB3 deubiquitinates and stabilizes SNAIL1. (A) Cell extracts were prepared from 4 luminal and 4 basal like subtypes of human breast cancer cell lines, and expression of SNAIL1, DUB3, E-cadherin and vimentin was analyzed by Western blotting. (B) MDA-MB-231 cells stably expressing control or DUB3 shRNAs were generated and Western blot was performed with the indicated antibodies. (C) Total RNA was isolated from cells in (B). mRNAs encoding SNAIL and β-actin were determined by reverse transcription-polymerase chain reaction (RT-PCR) and agarose gel electrophoresis. (D) MDA-MB-231 cells stably expressing control or DUB3 shRNAs were treated with vehicle or MG-132 (10 µM) for 1 hour and Western blot was performed with the indicated antibodies. (E-F) T47D and MCF-7 cells were infected with virus containing vector ("V"), FLAG-DUB3 ("WT") and the C89S ("CS") mutant, and Western blots were performed. (F) CHX pulse-chase assay was performed in cells. (G) Cells were cotransfected with indicated plasmids and treated with MG132 for 6 hours before cell lysates were boiled and immunoprecipitated with HA beads, and the polyubiquitylated SNAIL1 polypeptide was detected by an anti-ubiquitin antibody. (H) Cells were transfected with HA-SNAIL1 and treated with MG132 for 6 hours. Cell lysates were boiled and immunoprecipitated with HA beads and incubated with GST, GST-DUB3 or GST-DUB3 C89S mutant. The polyubiquitylated SNAIL1 polypeptide was detected by an anti-ubiquitin antibody.
Figure 3:
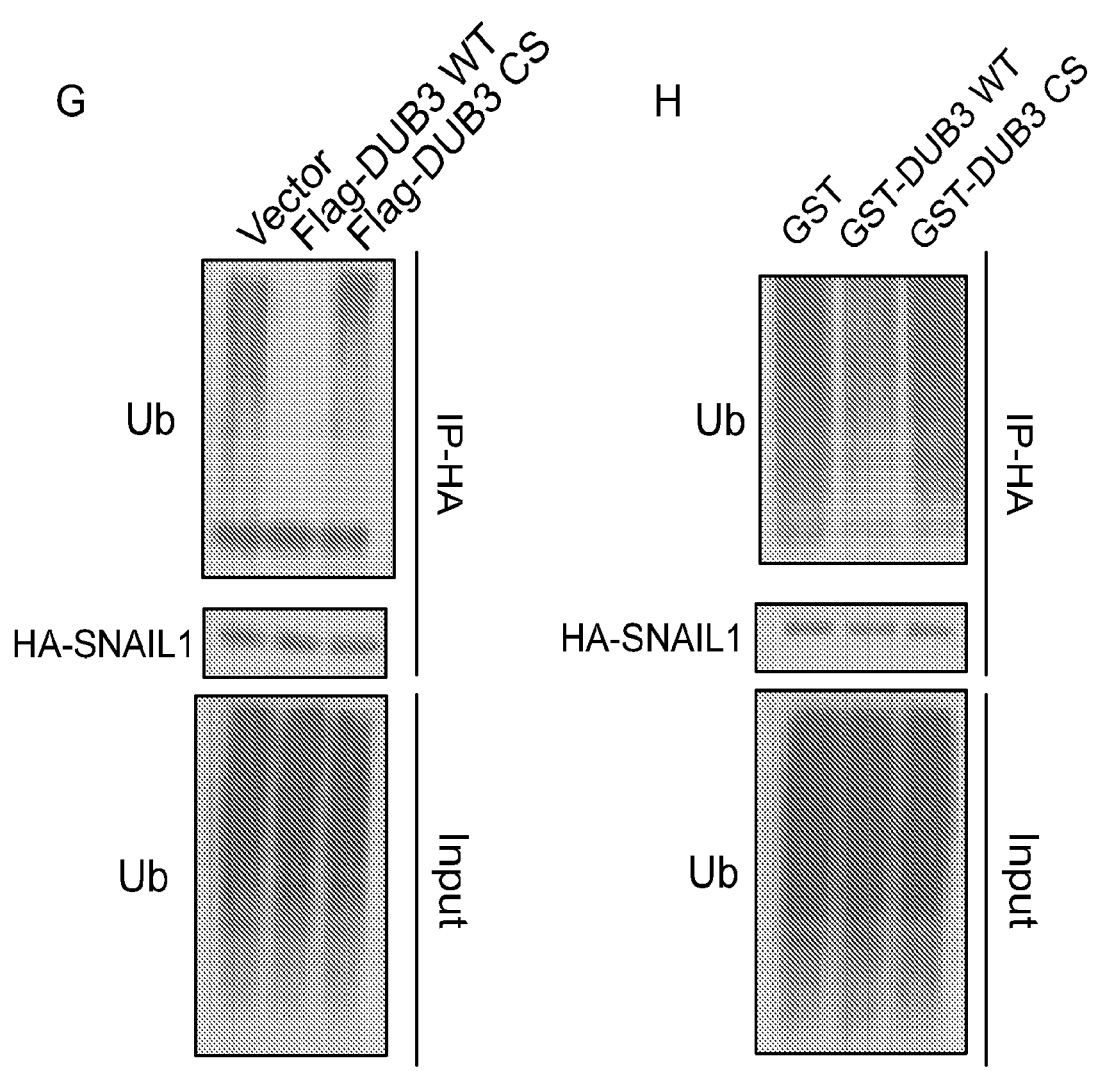

Example 2—DUB3 is a Bona Fide DUB Targeting SNAIL1 Polypeptide for Deubiquitination and Stabilization DUB3 and SNAIL1 polypeptide levels were detected in luminal and basal like breast cancer cell lines. As shown in FIG. 3A, DUB3 and SNAIL polypeptide levels are much higher in basal-like breast cancer cell lines. To directly test the function of DUB3 on endogenous SNAIL1 polypeptide turnover, DUB3 was knocked down with its specific shRNAs in MDA-MB-231 (FIG. 3B). Depletion of DUB3 significantly decreased SNAIL1 polypeptide level. The effect of DUB3 on SNAIL1 polypeptide turnover was not at the transcription level since no apparent difference of SNAIL1 mRNA was detected (FIG. 3C). On the other hand, MG132 treatment could rescue the decreased SNAIL1 polypeptide level in cells depleting DUB3 (FIG. 3D). Moreover, overexpression of wild type (WT) DUB3, but not the catalytically inactive C89S mutant in both MCF7 and T47D cells increased SNAIL1 polypeptide level (FIG. 3E). Furthermore, SNAIL1 polypeptide was less stable after DUB3 knockdown in a CHX pulse-chase assay (FIG. 3F). These results suggest that DUB3 regulate SNAIL1 stability. A de-ubiquitination Assay was performed by cotransfecting cells with WT DUB3 or the C89S mutant in the presence of MG-132. A significant decrease of polyubiquitinated SNAIL1 polypeptide was observed in cells transfected with WT DUB3, whereas the expression of C89S mutant was not able to decrease SNAIL1 ubiquitination (FIG. 3G). In addition, WT DUB3, but not the C89S mutant dramatically decreased SNAIL1 ubiquitination in vitro (FIG. 3H). Taken together, these results suggest that DUB3 is a bona fide DUB targeting SNAIL1 polypeptide for deubiquitination and stabilization.

Example 3—DUB3 Regulates EMT Through SNAIL1

Experimental and clinical evidence suggests that SNAIL1 promotes EMT. To investigate the potential function of DUB3 in this process, DUB3 was overexpressed in two luminal breast cancer cell lines MCF-7 and T47D. Expression of WT DUB3 decreased epithelial marker E-cadherin expression, gained mesenchymal marker (N-cadherin and Vimentin) expression, and converted luminal cells into basal-like phenotypes (FIG. 4A-B). To test whether DUB3 functions through SNAIL1 in promoting basal-like phenotype conversion, SNAIL1 shRNA was co-transfected with DUB3 in luminal cells. Depletion of SNAIL1 blocked the DUB3-induced downregulation of E-cadherin, morphological changes indicative of EMT and the basal-like phenotype conversion in these cells (FIG. 4A-B). Collectively, these results suggest that DUB3 regulates EMT by stabilizing SNAIL1.

Example 4—DUB3 Regulates Cell Migration and Invasion In Vitro and Cancer Metastasis in Vivo Through SNAIL1

Figure 4:
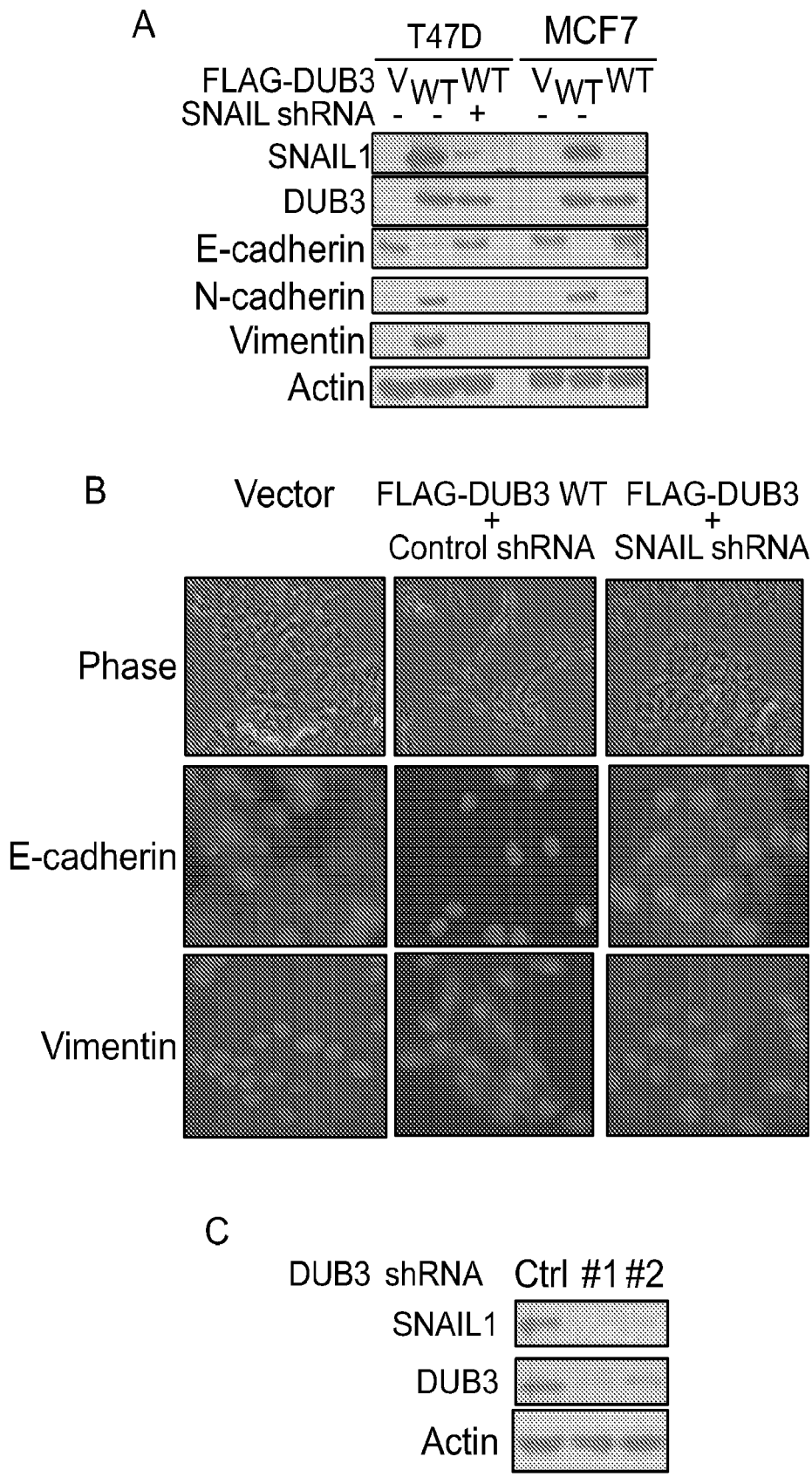
FIG. 4. DUB3 regulates EMT through SNAIL1. (A) T47D and MCF-7 cells were transfected with indicated plasmids and Western blots were performed with indicated antibodies. (B) T47D cells were transfected with indicated plasmids and cell morphological changes associated with EMT were shown in the phase contrast images. Expression of E-cadherin and vimentin was analyzed by immunofluorescence. Nuclei were visualized with DAPI staining (blue). (C-E) MDA-MB231 cells were stably transfected with control and DUB3 shRNAs (C). The migratory ability of cells was analyzed by wound healing assay (D). The invasiveness of cells was analyzed with a chamber invasion assay (E). Cells as C were injected into the tail vein of immunodeficient mice. After 6 weeks, the development of lung metastases was recorded using bioluminescence imaging (F) and quantified (G). After 12 weeks, mice were sacrificed and lung metastatic nodules were counted and quantified (H-I).
Figure 4:
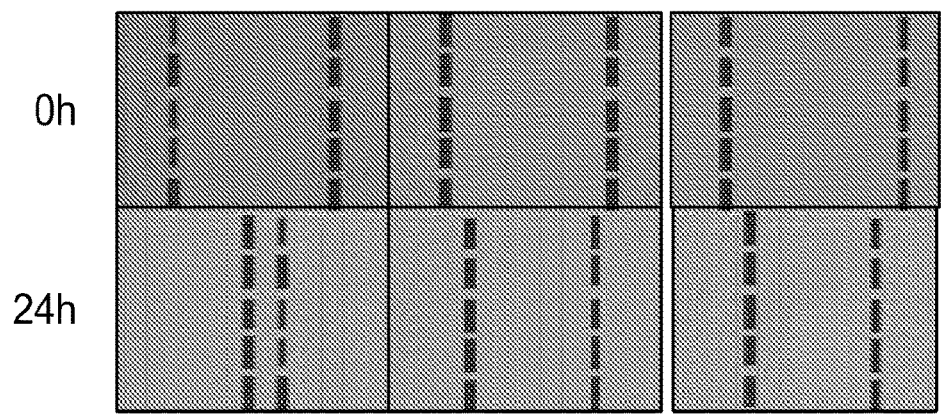
Figure 4:
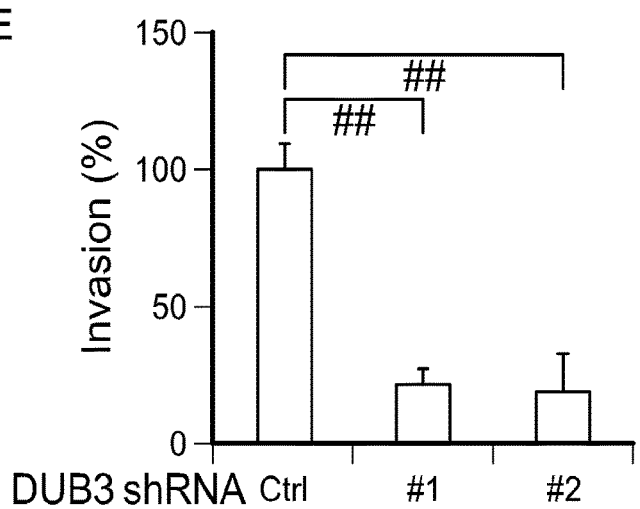
Figure 4:
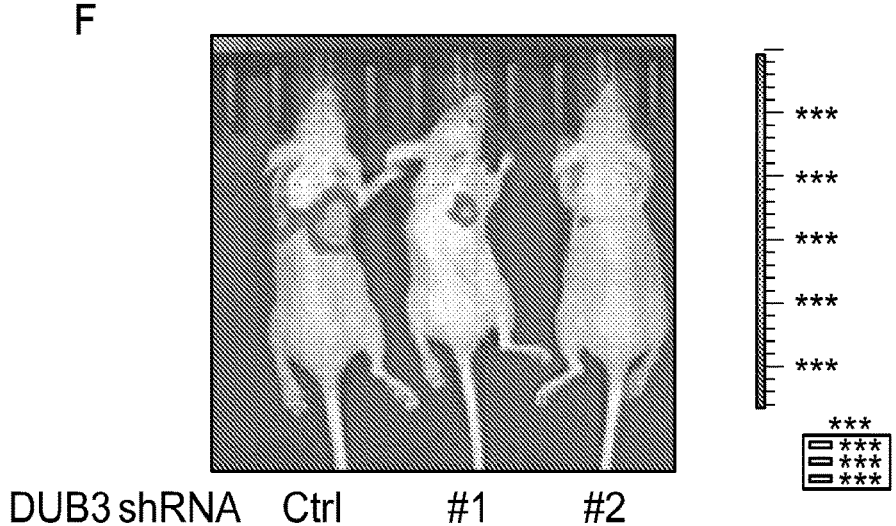
Figure 4:
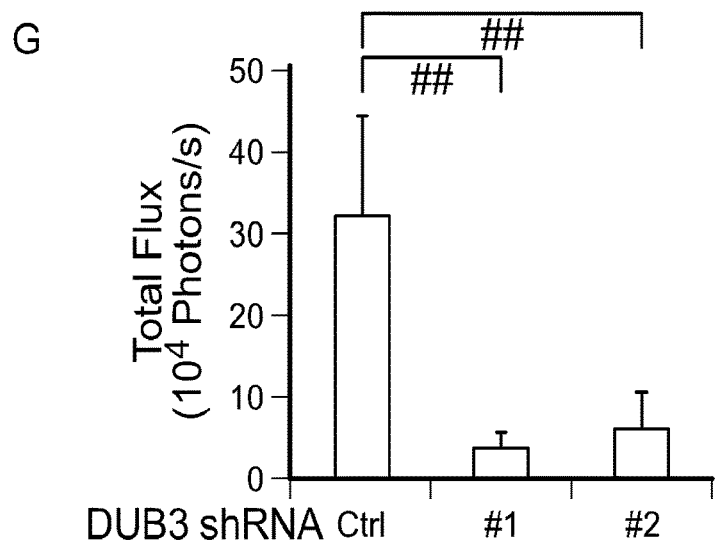
Figure 4:
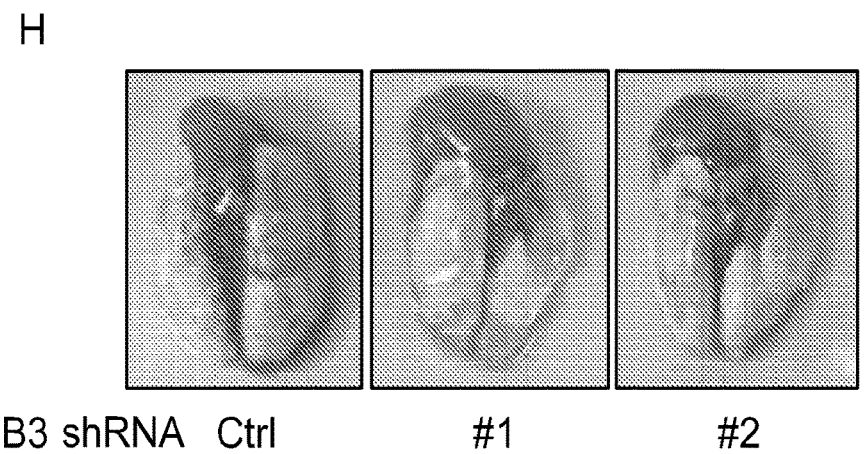
Figure 4:
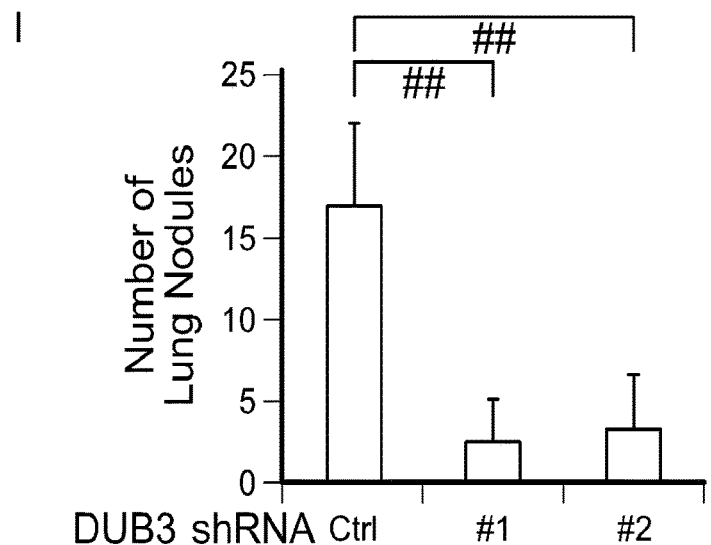
Figure 5:
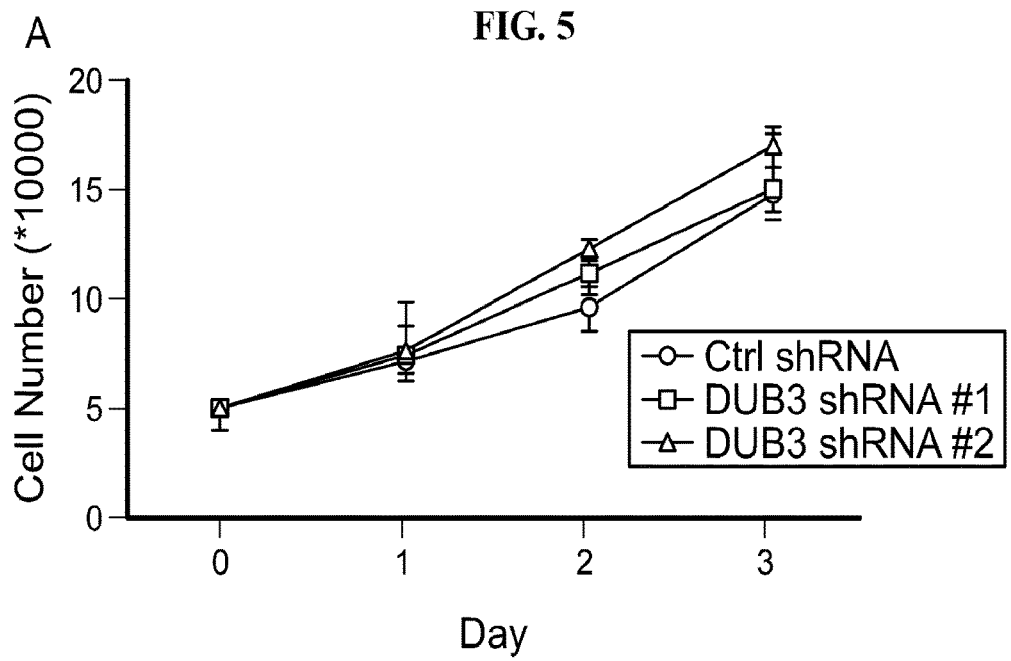
FIG. 5. DUB3 regulates the migratory activity of MDA-MB-231 cells via stabilizing SNAIL1. (A) MDA-MB-231 cells stably expressing control or DUB3 shRNAs were seeded in each well ($5 \times 10^4$/well) and cell numbers were counted every 24 hours. Data are represented as the mean±SD of four independent experiments. (B) MDA-MB-231 cells stably expressing control or DUB3 shRNAs were transfected with indicated constructs. Western blotting was performed with indicated antibodies. (C) The migratory ability of cells as in C was analyzed by a wound healing assay.
Figure 5:
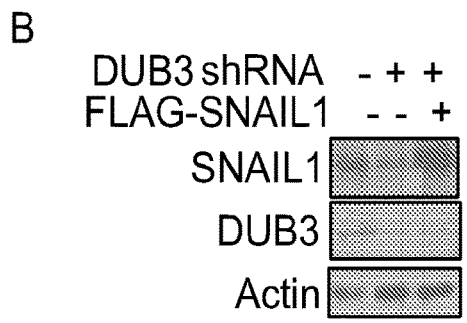
Figure 5:
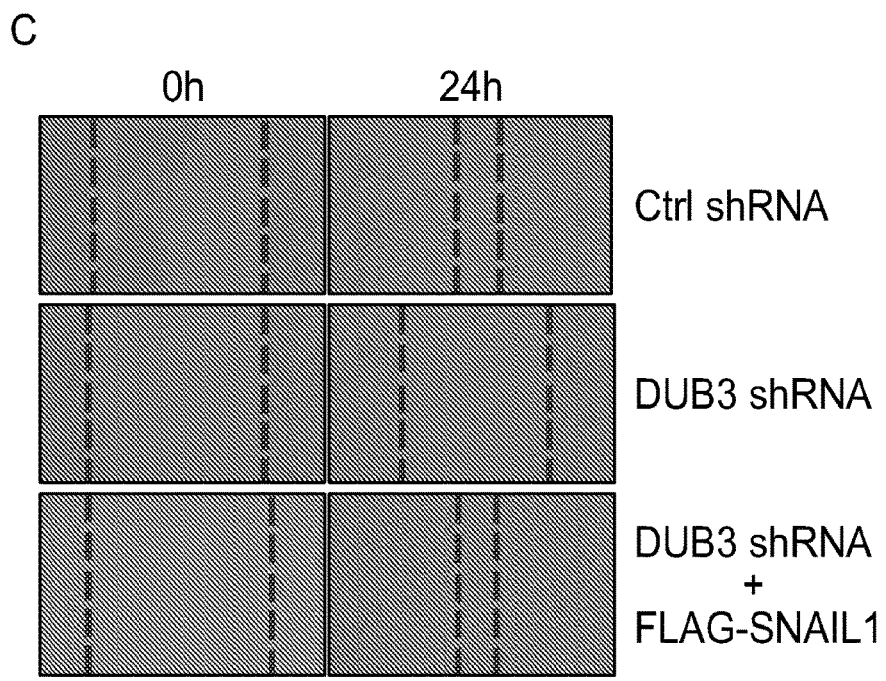

Although depletion of DUB3 has no apparent effect on cell growth (FIG. 5A), knockdown of DUB3 expression greatly inhibited the migratory ability and invasiveness of MDA-MB231 cells (FIG. 4C-E), which could be totally rescued by overexpression of SNAIL1 (FIG. 5B-C). Altogether, these results indicate that SNAIL1 is a factor for DUB3's effect on migration and invasion.

Figure 6:
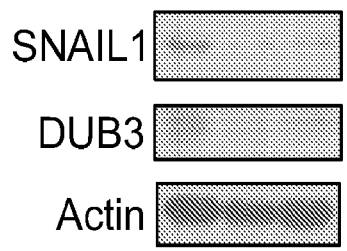
FIG. 6. Depletion of mDUB3 in melanoma cells regulates the migration and lung metastasis. (A) B16F10 cells were stably transfected with control and DUB3 shRNAs. Western blotting was performed with indicated antibodies. The migratory ability of cells was analyzed by a wound healing assay (B). Cells from A were injected into the tail vein of ICR-SCID mice. After 12 days, mice were sacrificed, and lung metastatic nodules were counted (C) and quantified (D). Data are represented as the mean±SD of 8 mice.
Figure 6:
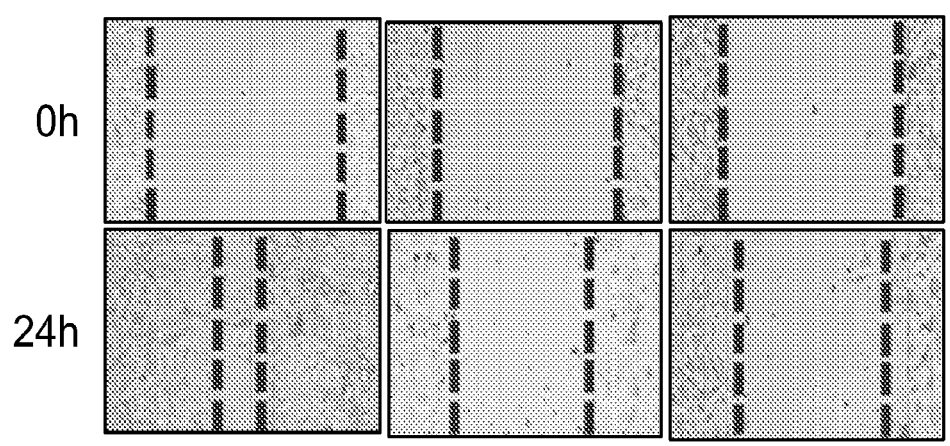
Figure 6:
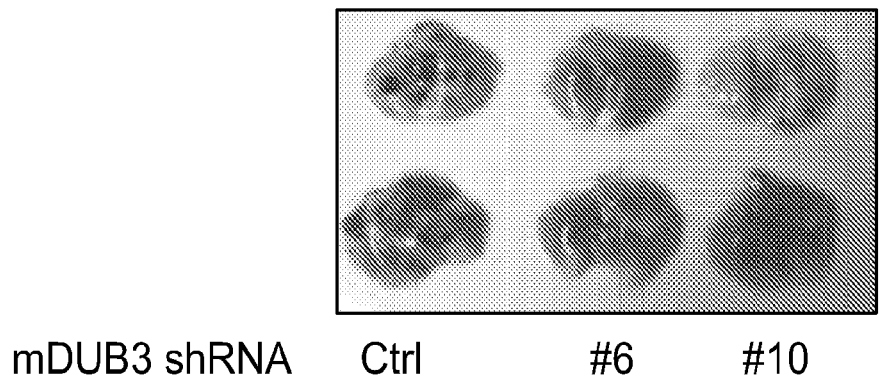
Figure 6:
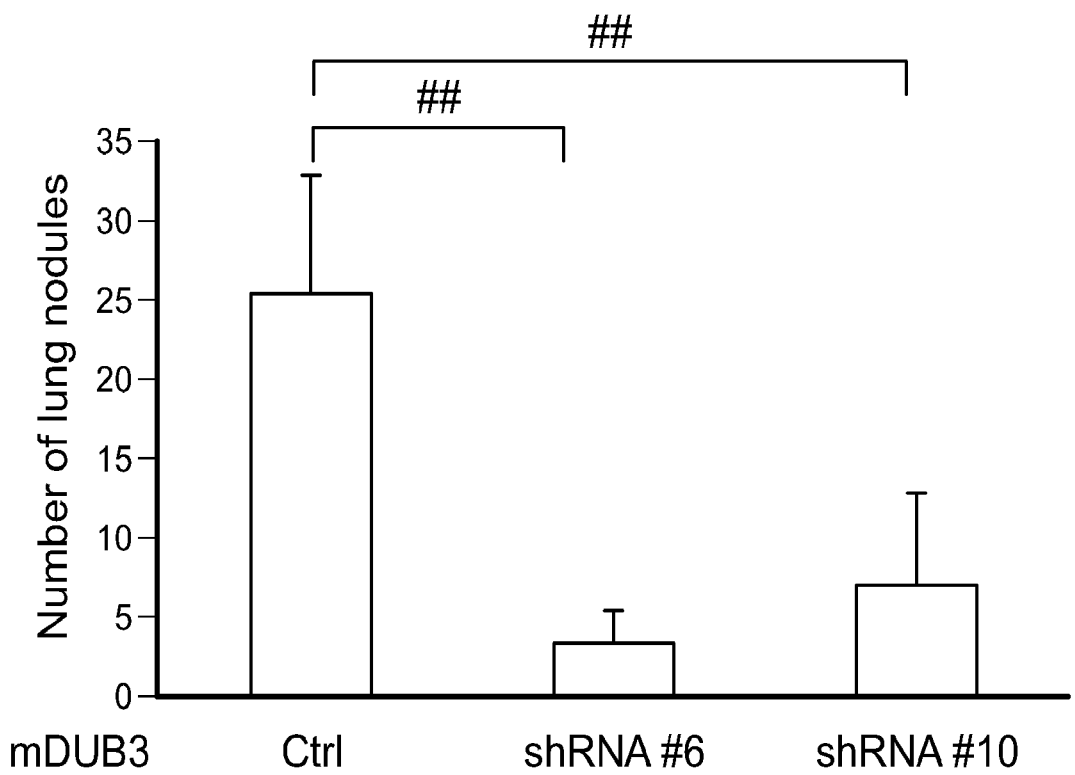

Using an experimental metastasis model, tumor cells were directly injected into the tail veil of immuno-deficient mice. Although same amount of MDA-MB-231 cells ($2\times10^6$) were directly injected into the tail veil of SCID mice, knockdown of DUB3 expression in MDA-MB-231 cells dramatically suppressed lung colonization in these mice, as determined by intensity of bioluminescence (FIG. 4F-G) and lung nodule counting (FIG. 4H-I). Similar to the observation in MDA-MB231 cells, knockdown of DUB3 expression in B16F10 cells also suppressed migration ability of these cells in vitro (FIG. 6A-B) and inhibited lung colonization in vivo (FIG. 6C-D). Together, these results demonstrate that DUB3 is important for cell migration, invasion, and lung colonization through stabilizing SNAIL1 to suppress E-cadherin expression.

Figure 7:
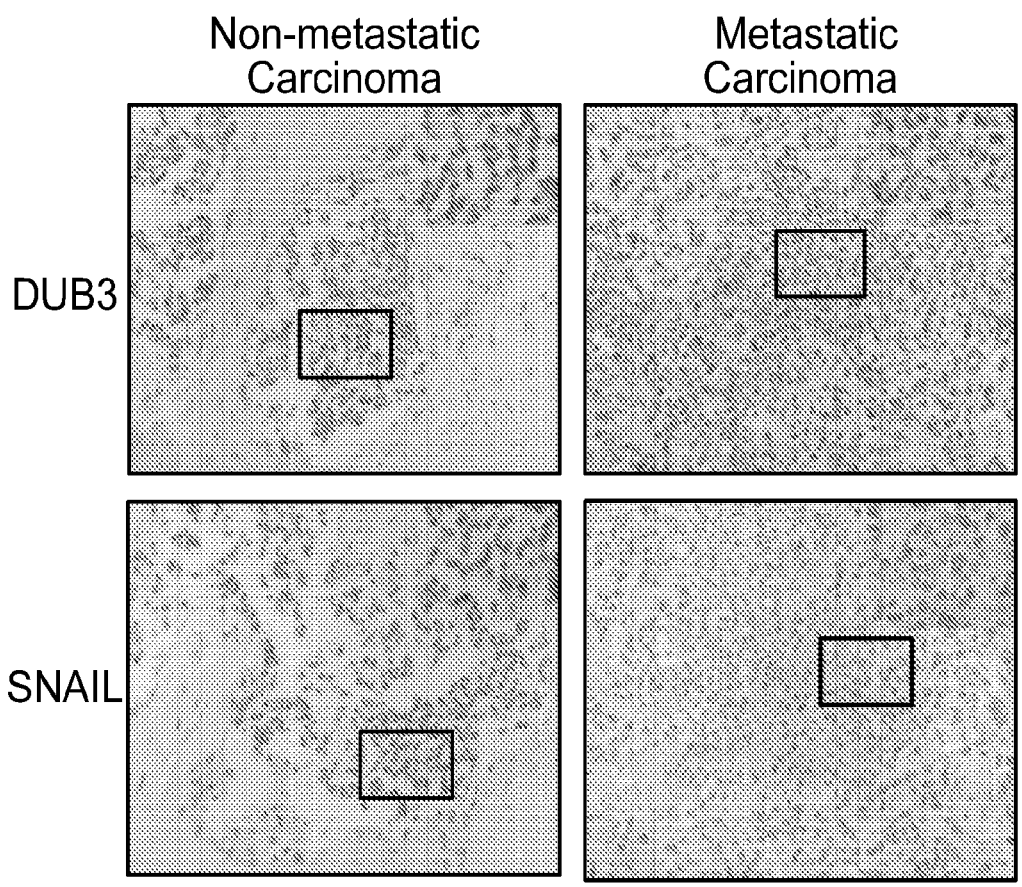
FIG. 7. DUB3 expression positively correlates with SNAIL1 expression in Clinical Breast Cancer Samples. (A) Representative images of immunohistochemical staining of DUB3 and SNAIL1 in normal and breast carcinomas. (B-C) Correlation study of the DUB3 (B) and SNAIL1 (C) expression levels with metastatic carcinoma. (D-E) Correlation study of DUB3 and SNAIL1 in metastatic carcinoma (D) and non-metastatic carcinoma (E). Staining score 0-1 was determined as low and 2-3 as high. Statistical significance was determined by chi-square testing. R: correlation coefficient.

Example 5—DUB3 is Positively Correlated to SNAIL1 in Clinical Breast Cancer Samples Results shown in FIG. 4 demonstrate DUB3's ability to increase breast cancer cell migration through targeting SNAIL1, supporting the hypothesis that DUB3 promotes breast carcinoma metastasis in patients. To further test this hypothesis, expression of DUB3 and SNAIL1 in breast cancer tissue samples was examined by using breast cancer tissue microarray. Notably, DUB3 polypeptide expression positively correlated with metastatic carcinoma (FIG. 7A-B, $P=2\times10^{-4}$, $R=0.363$). SNAIL1 polypeptide expression was also positively related with metastatic carcinoma (FIGS. 7A and 7C, $P=1\times10^{-4}$, $R=0.386$). Next, the correlation between DUB3 and SNAIL1 polypeptide levels was tested using the tissue microarray. Interestingly, DUB3 positively correlated with SNAIL1 in the metastatic carcinoma but not the non-metastatic carcinoma (FIG. 7D-E). These results suggest that both DUB3 and SNAIL1 are overexpressed and have a positive correlation with metastatic breast carcinoma. Altogether, these data indicate that the DUB3-SNAIL1 pathway might be not only a marker of progression of breast cancer and melanoma, but also a suitable target for therapy.

Example 6—CDK 4/6 Phosphorylates Ser41 of DUB3

Figure 8:
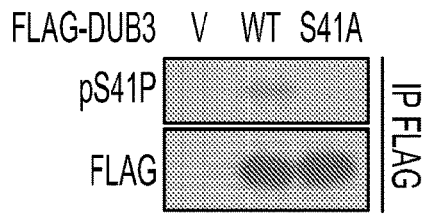
FIG. 8. CDK 4/6 phosphorylates DUB3 at Ser 41. (A) DUB3 phosphorylation sites were analyzed by mass spectrometry. If the Ascore values for Ascore Seq_A are above 19, then the location is considered confidently assigned (indicated with pink cell backgrounds). (B) Cells were transfected with indicated plasmids and cell lysates were subjected to immunoprecipitation with an anti-FLAG antibody and Western blotting was performed. (C) Cells were transfected with indicated plasmids and were treated with vehicle, or pan-CDK inhibitor (Roscovitine 5 μM) or CDK 4/6 inhibitor (PD0332991 10 μM). The phosphorylation of Ser41 was examined. (D) CDK 4/6 phosphorylates DUB3 in vitro. Bacterially expressed GST and GST-DUB3 fusion polypeptides were incubated with active CDK4 or CDK6 in the presence of [γ-32P]ATP. Polypeptides were resolved by SDS-PAGE, and phosphorylated polypeptides were visualized with autoradiography. (E) Vector or FLAG-DUB3 were transfected in cells stably expressing indicated shRNA. The phosphorylation of Ser41 in DUB3 was then examined.
Figure 8:
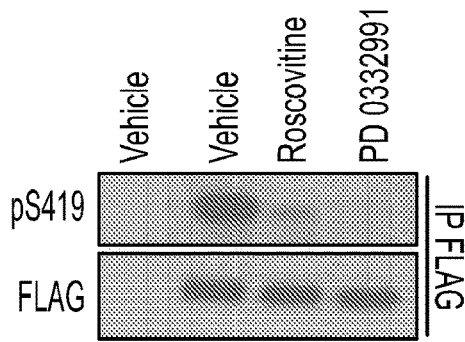
Figure 8:
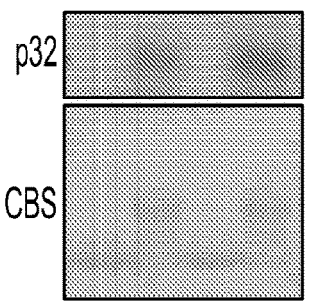
Figure 8:
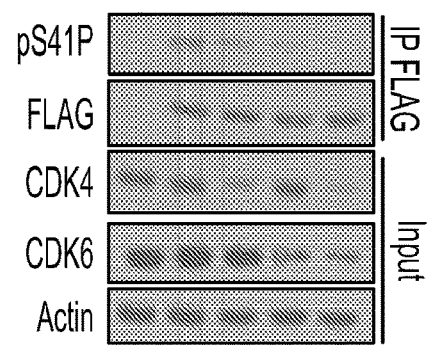
Figure 9:
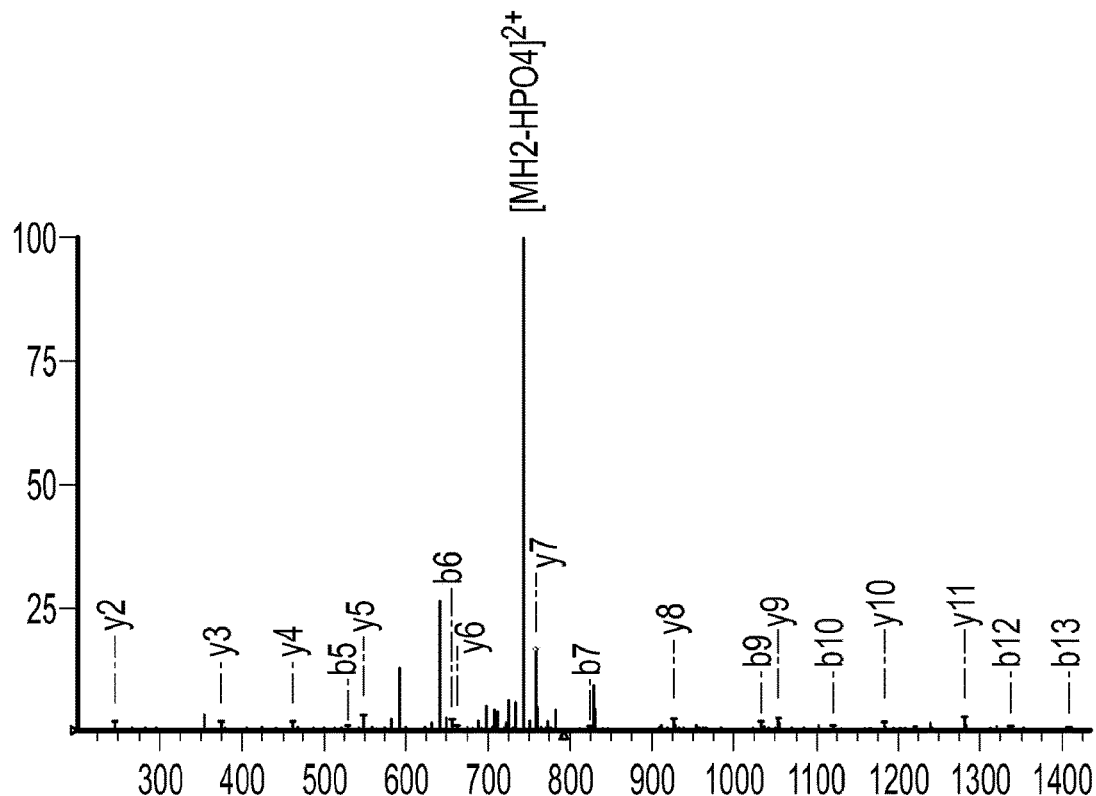
FIG. 9. Identification of Ser41 phosphorylation in DUB3 by mass spectrometry analysis.

To further investigate how the DUB3-SNAIL1 pathway is regulated, MDA-MB-231 cells stably expressing FLAG-DUB3 were generated to perform tandem affinity purification and mass spectrometry analysis of potential phosphorylation events in DUB3. It was discovered that Ser41 is a major phosphorylation site in DUB3 as shown in FIG. 8A and FIG. 9. A pSer41 specific antibody was generated to further study the phosphorylation of Ser41 in cells. HEK293T cells were transfected with WT DUB3 or the S41A mutant. As shown in FIG. 8B, WT DUB3 was phosphorylated in cells. However, S41A mutation completely abrogated the phosphorylation of DUB3 at this site, indicating the specificity of this antibody. Since Ser41 is located in a CDK consensus phosphorylation motif, it was tested whether CDK mediates this phosphorylation in DUB3. Cells were transfected with FLAG-DUB3 WT and were treated with a pan CDK inhibitor (Roscovitine) or a selective inhibitor of CDK 4/6, PD0332991 (Palbociclib, Pfizer). CDK inhibition dramatically reduced the phosphorylation of DUB3 at Ser41 (FIG. 8C). Next, it was tested whether CDK 4/6 could directly phosphorylate DUB3. GST or GST-DUB3 (aa 1-128) were incubated with active CDK4 or CDK6, and an in vitro kinase assay was performed. As shown in FIG. 8D, both CDK4 and CDK6 directly phosphorylated DUB3 in vitro. Furthermore, depletion of CDK4 or CDK6 in cells only partially decreased the phosphorylation of DUB3, while double knockdown of CDK4 and CDK6 almost completely abrogated DUB3 phosphorylation (FIG. 8E). These findings provide evidence that Ser41 is a major CDK 4/6-mediated phosphorylation site of DUB3.

Figure 10:
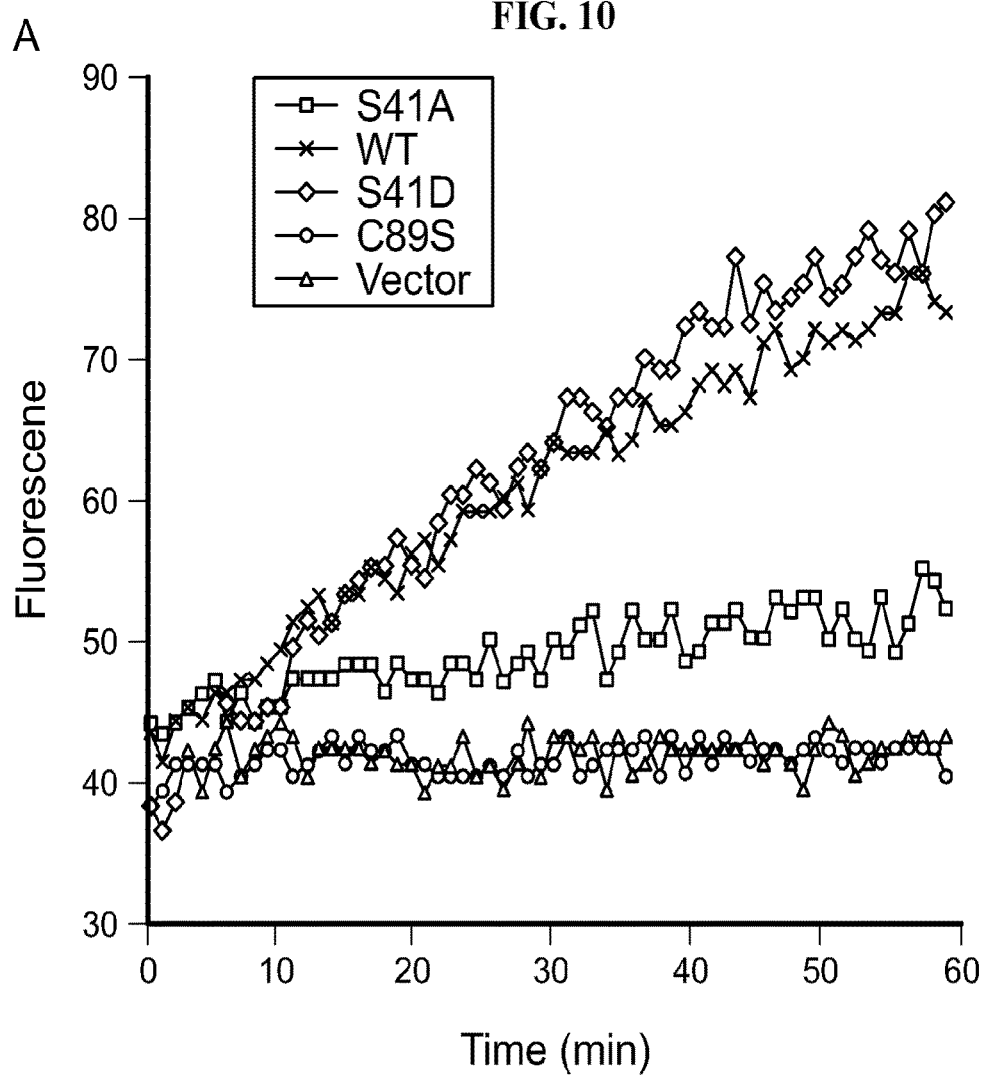
FIG. 10. Ser41 phosphorylation regulates DUB3 activity. (A) Cells transfected with indicated constructs were lysed and co-immunoprecipitations experiments were performed using anti-FLAG antibody. The immunoprecipates were eluted by FLAG-peptide containing buffer and the activities of DUB3 were assayed using Ubiquitin-AMC (Ub-AMC) as a substrate. (B) The eluates were detected with anti-FLAG antibody. (C) MDA-MB-231 cells were treated with either vehicle or PD0322991 for indicated periods. Western blotting was performed with indicated antibodies.
Figure 10:
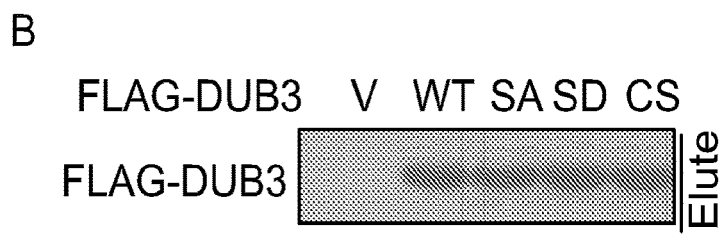
Figure 10:
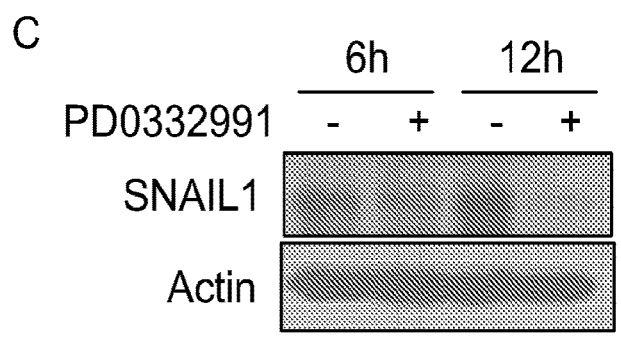
Figure 11:
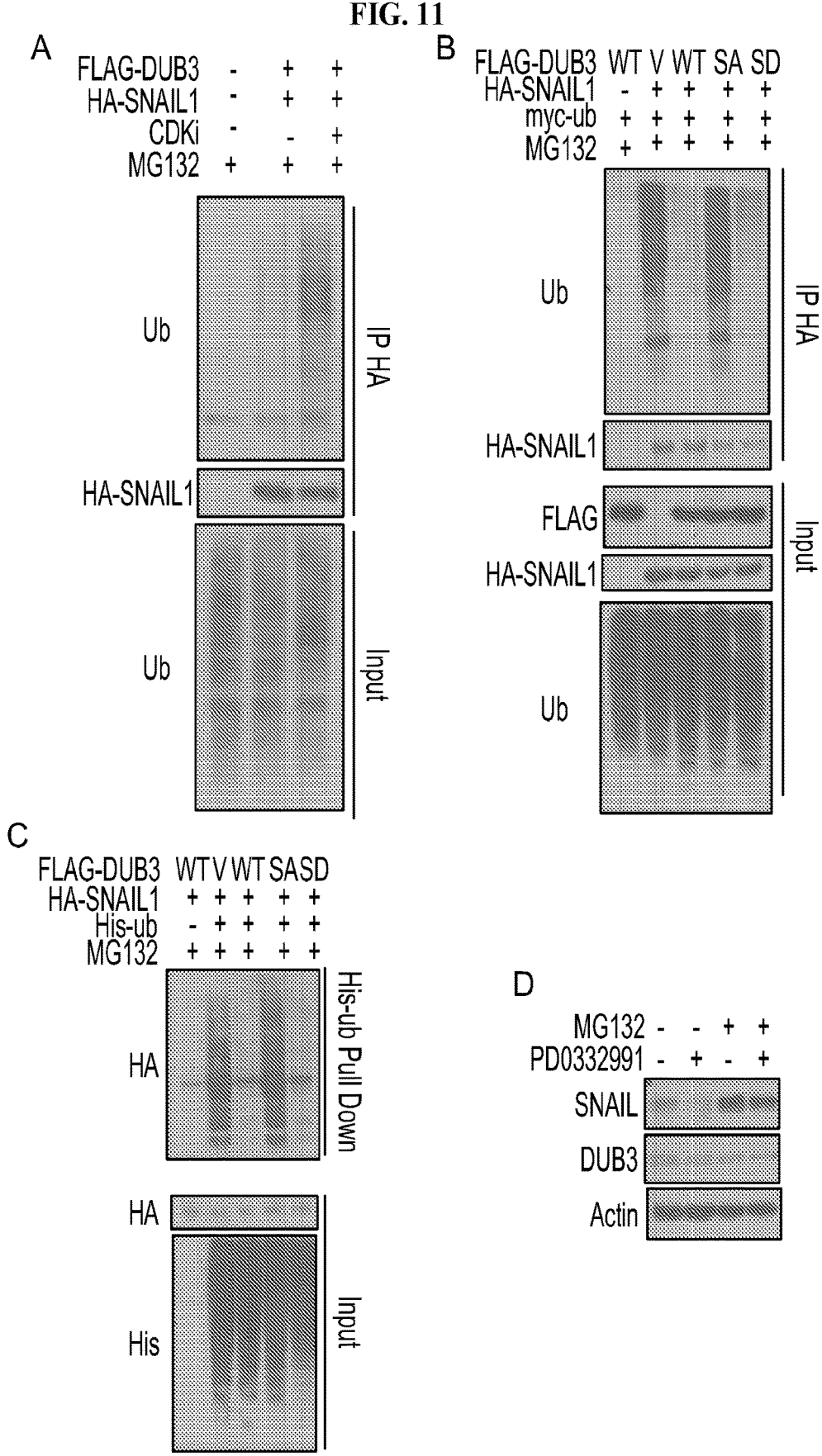
FIG. 11. Phosphorylation of Ser41 regulates DUB3 activity. (A) Cells were cotransfected with indicated plasmids and treated with vehicle or CDK 4/6 inhibitor (PD0332991 10 μM). Cell lysates were boiled and immunoprecipitated with HA beads and immunoblotted as indicated. (B) Cells were transfected with indicated plasmids and the polyubiquitylated SNAIL1 polypeptide was examined by Western blotting. (C) Cells were cotransfected with indicated plasmids and Ni-NTA beads were used to pull down His-tagged ubiquitin, and the polyubiquitylated SNAIL1 polypeptide was examined by Western blotting. (D) MDA-MB-231 cells were treated with vehicle or PD0332991 in the absence or presence of MG-132. Western blotting was performed as indicated. (E) Cells were treated with vehicle or PD0332991 for 12 hours and CHX pulse-chase assay was performed. (F) Cells were transfected with indicated plasmids and Western blotting was performed as indicated. (G) The migratory abilities of cells were analyzed by a wound healing assay. (H-I) Cells stably expressing DUB3 shRNA were transfected with the FLAG-DUB3 S41D or S41A mutant and were injected into the tail vein of ICR-SCID mice. After 12 weeks, mice were sacrificed and the development of lung metastases was determined by counting and quantifying lung metastatic nodules.
Figure 11:
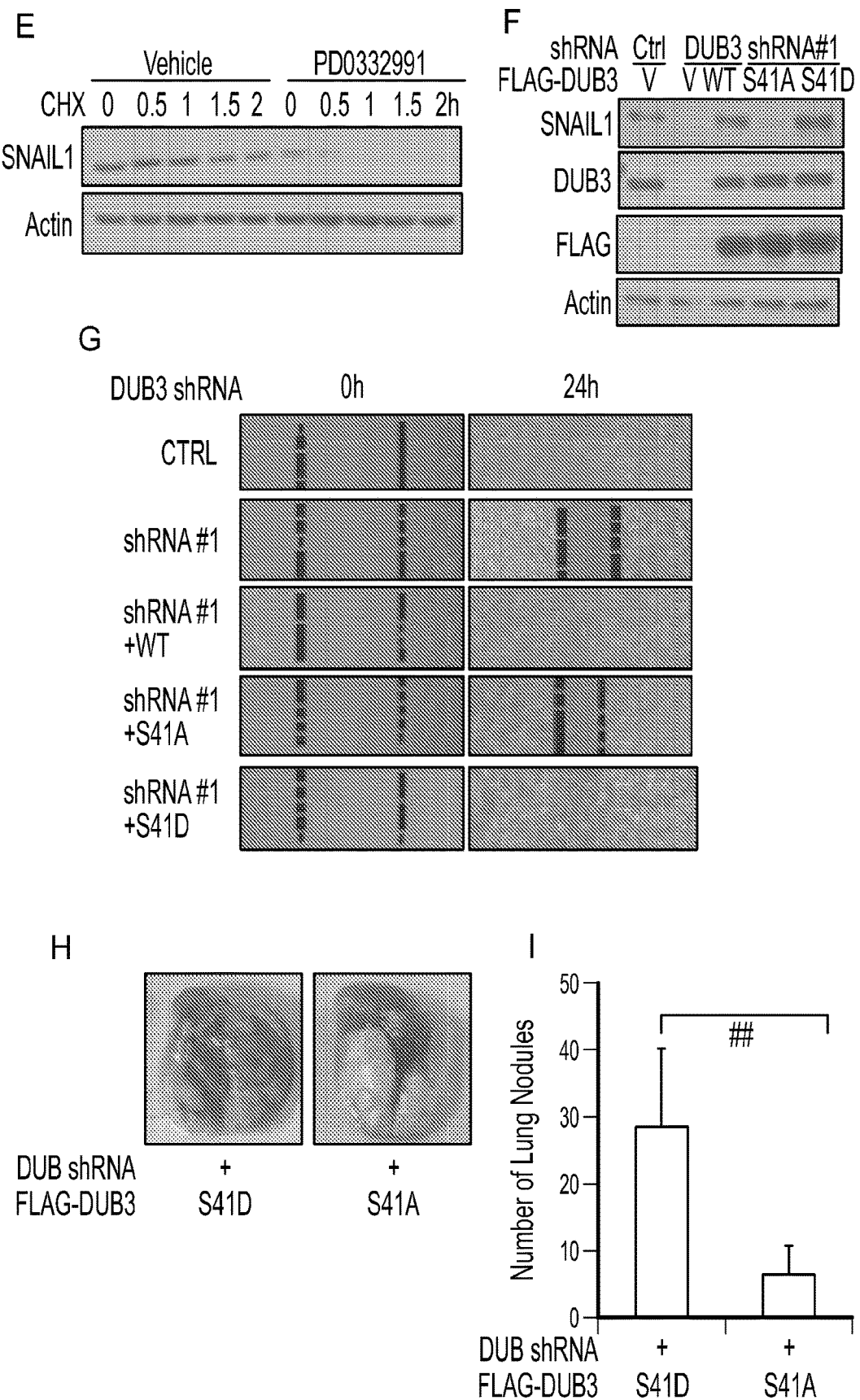

Example 7—CDK 4/6 Dependent Phosphorylation of Ser-41 is Critical for DUB3 Mediated SNAIL1 Stabilization To test whether CDK 4/6-mediated phosphorylation affects DUB3 activity, WT DUB3, the S41A mutant, or the S41D mutant (a phospho-mimic mutant) were transfected into cells and their activity toward Ubiquitin-AMC (Ub-AMC) was examined. Compared to the S41A mutant, WT DUB3 and the S41D mutant showed much higher activity towards Ub-AMC (FIG. 10A-B). This suggests that Ser41 phosphorylation increases the deubiquitinase activity of DUB3. To test how CDK 4/6 and Ser41 phosphorylation of DUB3 affects SNAIL1 ubiquitination, cells were transfected with FLAG-DUB3 and HA-SNAIL1. The cells were then treated with either vehicle or the CDK 4/6 inhibitor PD0332991, and SNAIL1 ubiquitination was determined. As shown in FIG. 11A, SNAIL1 ubiquitination was stronger in cells treated with PD0332991 compared to vehicle, suggesting that CDK 4/6 activity is important for suppression of SNAIL ubiquitination. To further test whether phosphorylation of Ser41 on DUB3 could affect the ubiquitination of SNAIL1 in cells, WT DUB3, the S41A mutant, or the S41D mutant were transfected into cells and SNAIL1 ubiquitination was checked. As shown in FIG. 11B-C, both WT DUB3 and the S41D mutant efficiently decreased the ubiquitination of SNAIL1. The S41A mutant, however, failed to decrease ubiquitination of SNAIL1. Collectively, these results suggest that phosphorylation of Ser41 is associated with the deubiquitinase activity of DUB3 toward SNAIL1.

Figure 12:
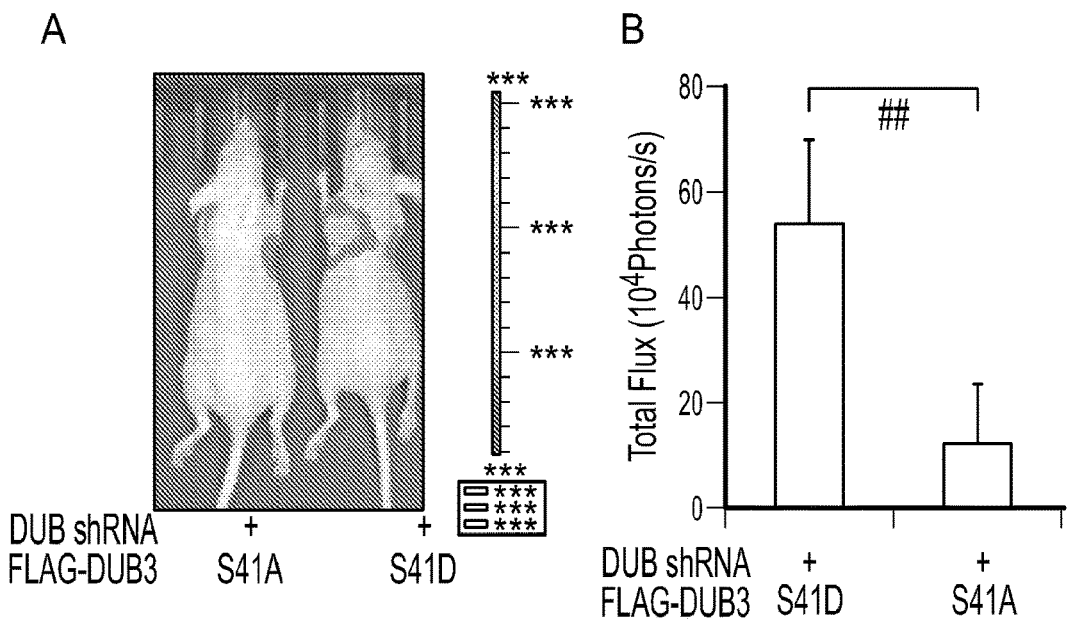
FIG. 12. Ser41 phosphorylation regulates cancer metastasis. (A) FLAG-DUB3 S41A or S41D mutants were transfected in MDA-MB231 cells stably expressing DUB3 shRNA. Cells were injected into the tail vein of immunodeficient mice. After 6 weeks, the development of lung metastases was recorded using bioluminescence imaging (A) and quantified (B).

It was next determined whether CDK 4/6 inhibition affects SNAIL1 turnover. As shown in FIG. 11D and FIG. 10C, CDK 4/6 inhibitor PD0332991 treatment significantly reduced the level of SNAIL1 polypeptide, which was reversed by MG-132 treatment. Inhibition of CDK 4/6 by PD0332991 also dramatically decreased SNAIL1 polypeptide stability in a CHX pulse-chase assay (FIG. 11E). To further test whether phosphorylation of Ser41 on DUB3 could affect the polypeptide level of SNAIL1 in cells, shRNA-resistant WT DUB3, S41 and S41D mutants were reconstituted in DUB3 knockdown cells and the level of SNAIL1 was determined. As shown in FIG. 11F, DUB3 knockdown efficiently decreased SNAIL1 polypeptide. WT DUB3 and the S41D mutant rescued the SNAIL1 polypeptide level, while the S41A mutant failed to do so. Moreover, knockdown of DUB3 expression greatly inhibited the migratory ability of MDA-MB231 cells. WT DUB3 and the S41D mutant, but not the S41A mutant, rescued this phenotype (FIG. 11G). Results from in vivo metastasis model showed that the reconstitution of the S41D mutant in MDA-MB-231 cells depleting DUB3 causes stronger lung colonization than the S41A mutant, as determined by lung nodules counting (FIG. 11H-I) and by intensity of bioluminescence (FIG. 12A-B). These results establish that CDK 4/6-mediated phosphorylation of DUB3 is involved in DUB3 activity and SNAIL1 stability.

Example 8—CDK 4/6 Inhibitor PD0332991 Decreases Human Cancer Metastasis

Figure 13:
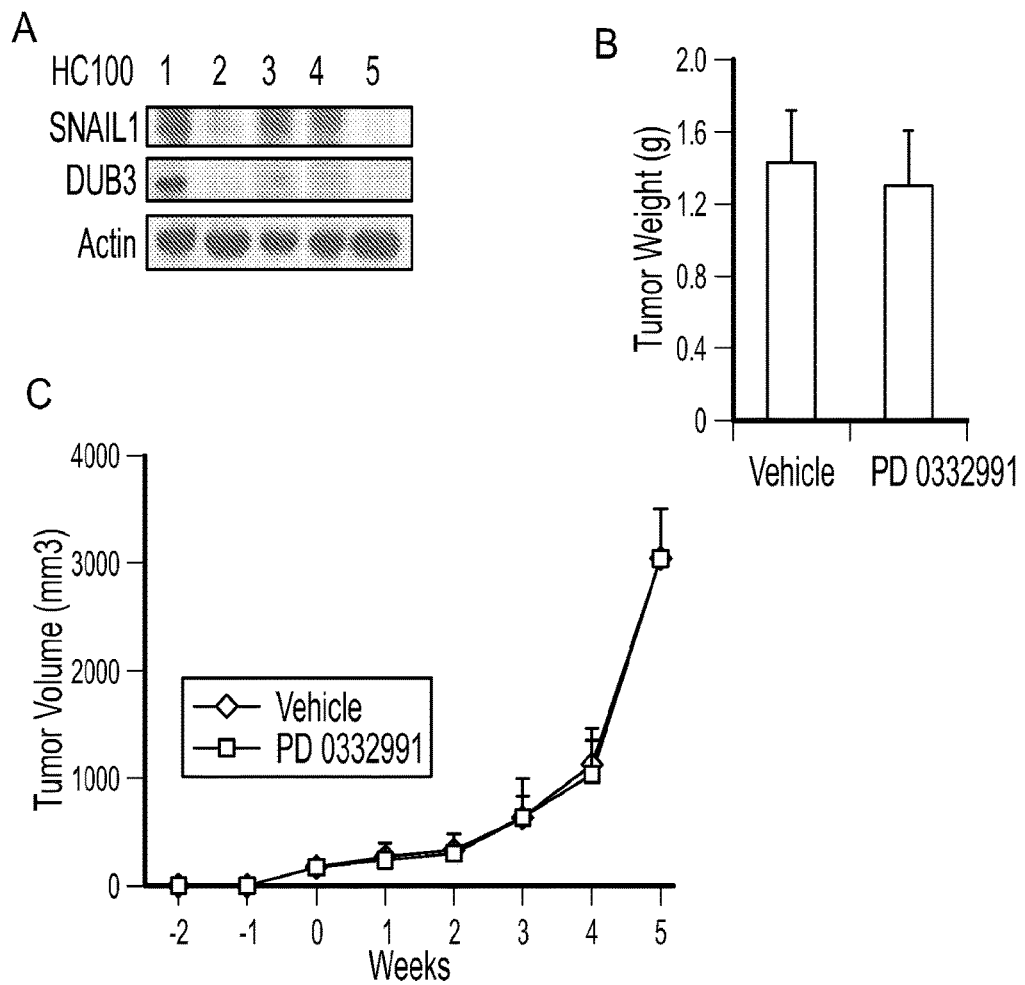
FIG. 13. CDK 4/6 inhibition inhibits cancer metastasis. (A) DUB3 and SNAIL1 polypeptide levels in a subset of human breast tumor biopsy samples were examined. (B) Passage 3 tumors from HCI001 were used to test the effect of PD0332991 on metastasis. When primary tumors reached 100-150 mm$^3$, mice were randomized and treated either with saline or PD0332991 for five weeks (n=8). Tumor weights were measured after mice were sacrificed (B). Tumor volumes were measured every week (C). After mice were sacrificed, liver (D-F) and lung (G-I) metastatic nodules were examined macroscopically or detected in paraffin-embedded sections stained with H&E. (J) The working model to illustrate that CDK 4/6 phosphorylation-dependent activation of DUB3 regulates EMT and metastasis through SNAIL1.
Figure 13:
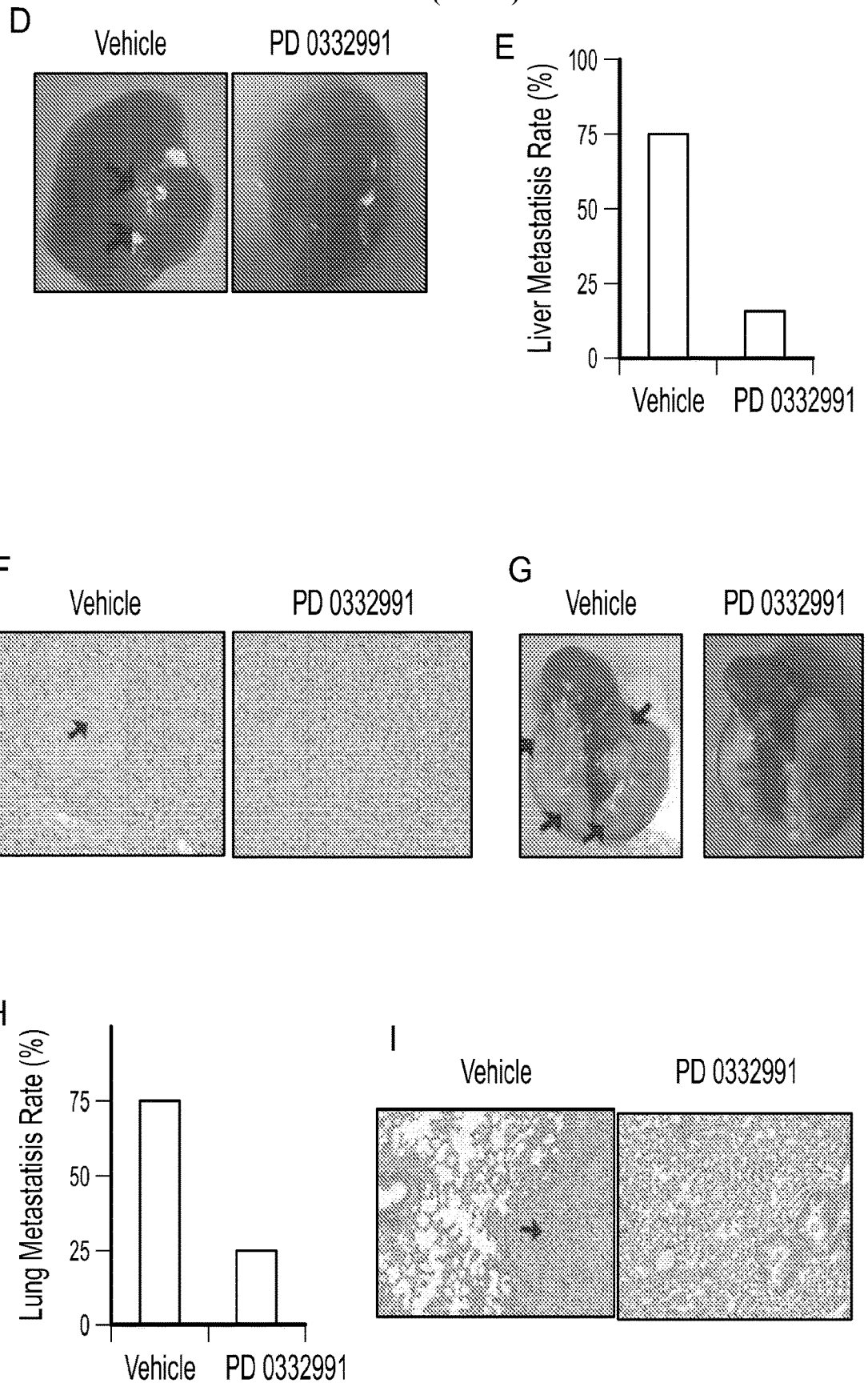
Figure 13:
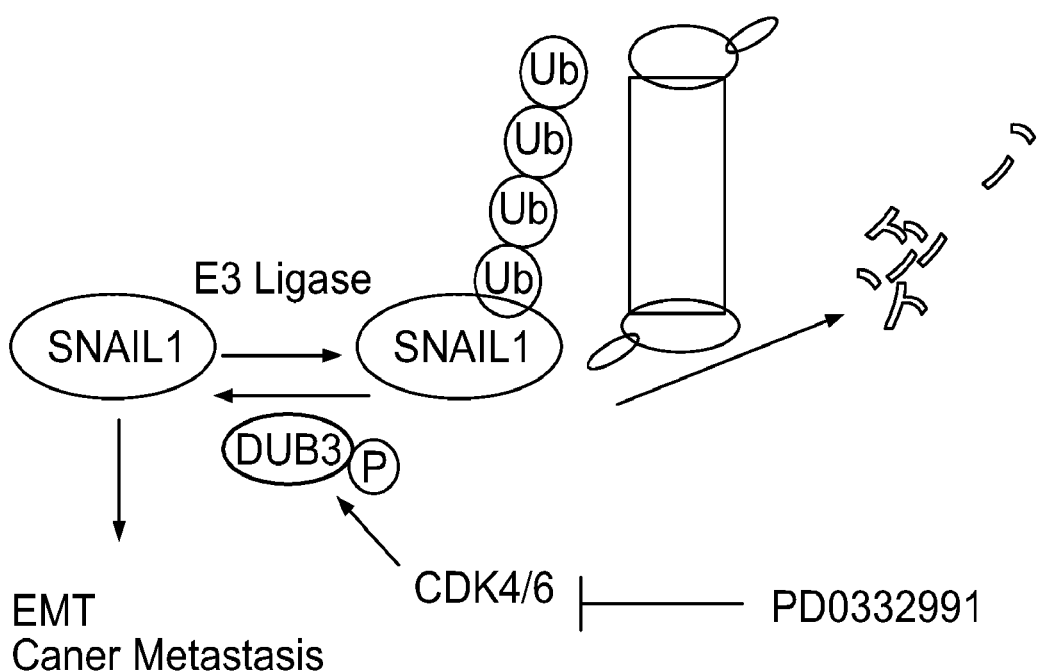

The results provided herein indicate that DUB3 stabilizes SNAIL1 polypeptide through deubiquitinating SNAIL1 and CDK 4/6 activity is involved in SNAIL1 stabilization. PD0332991 was tested in a patient-derived xenograft (PDX) model generated from an estrogen receptor-negative, progesterone receptor-negative, human epidermal growth factor receptor 2-negative (ER-PR-_HER2-) high-grade invasive ductal carcinoma by the Breast Cancer Genome-Guided Therapy study (BEAUTY) in Mayo Clinic. DUB3 and SNAIL1 levels were detected and correlated in a subset of human breast cancer samples from the BEAUTY project (FIG. 13A). Metastasis in immunodeficient mice implanted with human breast tumor biopsy sample HCI001 included liver, lung, as well as ovary reflecting the metastatic pattern in the donor patient Briefly, freshly operated human breast tumor biopsy sample HCI001 was implanted at the flank of immunodeficient mice. When tumor size reached 1000 mm$^3$, mice were sacrificed and tumor fragments (3 mm$^3$) were re-transplanted into mammary fat pads of additional mice. Passage 3 tumors were used to test the effect of PD0332991 on metastasis. When primary tumors reached 100-150 mm$^3$, mice were randomized and treated either with saline or PD0332991. The administration of PD0332991 did not affect the primary tumor growth as shown in FIGS. 13B-C. However, PD0332991 significantly decreased liver (1/8 vs 6/8) and lung (2/8 vs 6/8) metastasis compared to saline group (FIGS. 13D-F, G-I). The metastasis in lung and liver was confirmed by IHC (FIGS. 13F and I). These results from PDX models demonstrated that CDK 4/6 inhibitor PD0332991 could inhibit TNBC metastasis in vivo.

Figure 14:
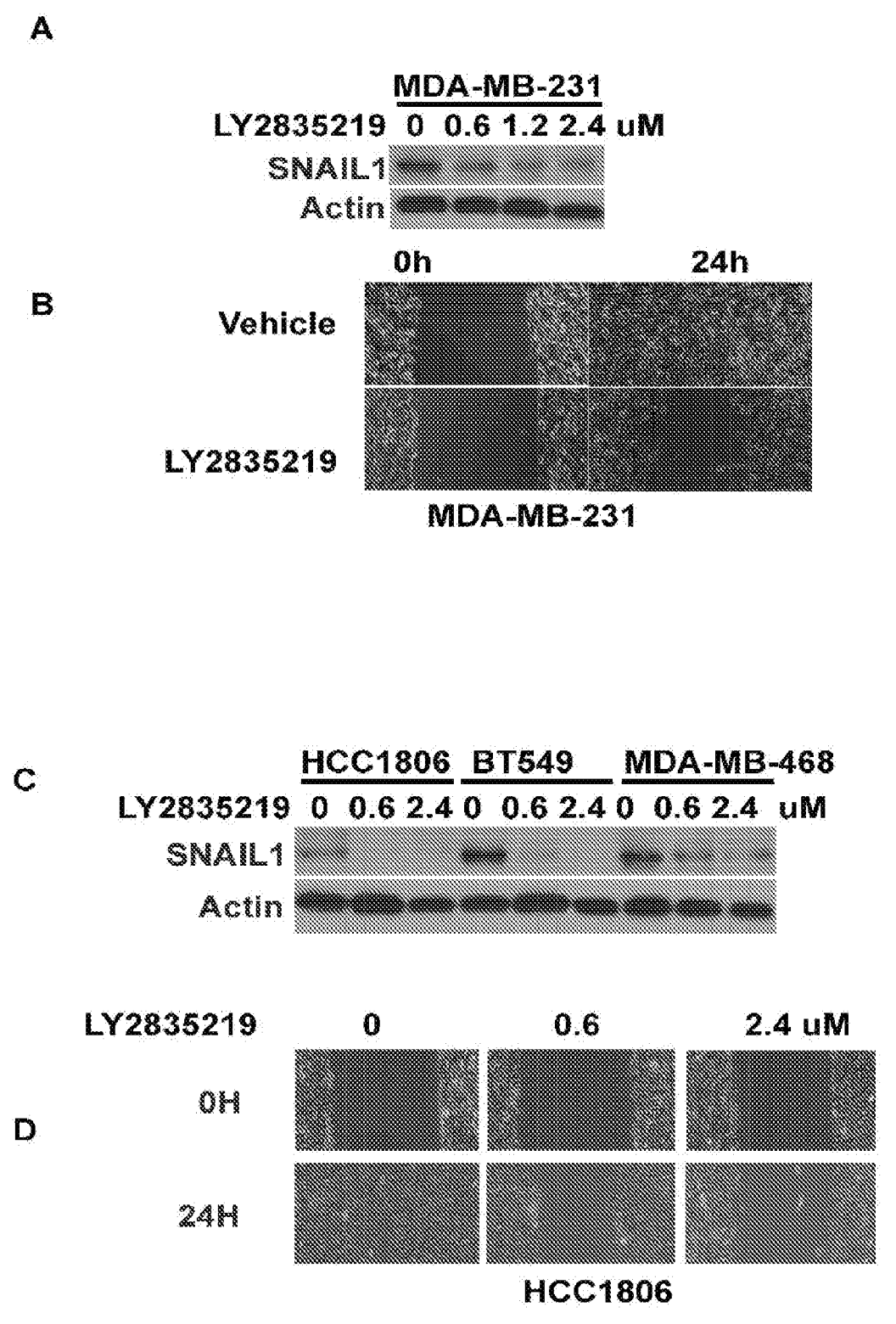

Example 9—CDK 4/6 Inhibitor LY2835219 Decreases SNAIL1 Polypeptide Level and Inhibits the Migratory Activity of TNBC Cells To test the broader applicability of other CDK 4/6 inhibitors to inhibit metastasis in TNBC cells, additional experiments were performed with a different CDK 4/6 inhibitor, LY2835219 (Abemaciclib, Eli Lilly). As shown in FIG. 14A-D, LY2835219 also effectively inhibited SNAIL polypeptide levels and the migratory activity of the cells. MDA-MB-231 were treated with vehicle or LY2835219 at the indicated concentration for 24 hours and SNAIL1 polypeptide levels were detected by Western blotting (FIG. 14A). Increasing concentrations of LY2835219 progressively decreased expression of SNAIL1 (FIG. 14A). MDA-MB-231 were treated with vehicle or LY2835219, and the migration ability of cells were measured by wound healing assay. LY2835219 effectively inhibited migratory activity of these cells (FIG. 14B). HCC1806, BT549, and MDA-MB-468 cells were treated with vehicle or LY2835219 at the indicated concentration for 24 hours and SNAIL1 polypeptide levels were detected by Western blotting (FIG. 14C). Increasing concentrations of LY2835219 progressively decreased expression of SNAIL1 in each of these cells (FIG. 14C). HCC1806 cells were treated with vehicle or LY2835219 and the migration ability of cells were measured by wound healing assay. LY2835219 effectively inhibited migratory activity of these cells (FIG. 14D).

Example 10—Experimental Procedures

Cell Culture, Plasmids and Antibodies

293T, MDA-MB-231, B16F10, MCF-7 and T47D cells were cultured in DMEM supplemented with 10% fetal bovine serum (FBS). DUB3 and SNAIL1 were cloned into pIRES-EGFP, pCMV-HA, pLV.3-FLAG, pGEX4T-1 and PET28A vector. All site mutants were generated by site-directed mutagenesis (Stratagene) and verified by sequencing. DUB3 and SNAIL1 shRNA were purchased from Sigma.

Antibodies against SNAIL1, E-cadherin, N-cadherin, and Vimentin were purchased from Cell Signaling. Anti-FLAG (m2), anti-HA, and anti-β-actin antibodies were purchased from Sigma. Ubiquitin, Cdk4, and Cdk 6 antibodies were purchased from Santa Cruz. Rabbit anti-DUB3 antibody and pSer41 were generated by immunizing rabbits with GST-fusion polypeptide and phospho-peptide respectively, and then affinity purified.

Immunofluorescence (IF) Staining

Cells were seeded onto glass coverslips for the experiment. Cells were washed with PBS, fixed with 4% formaldehyde for 10 min, permeabilized with 0.1% Triton X-100 for 5 min, blocked with 5% goat serum for 1 hour, incubated with primary antibodies for 1 hour and then with secondary antibodies. The antibodies used in the IF stainings were E-cadherin (1:200 cell signaling) and Vimentin (1:500 cell signaling).

Experimental Metastasis Model

Female SCID mice (6 weeks old) were purchased from the National Cancer Institute and maintained and treated under specific pathogen-free conditions. Experiments were performed under institutional approval. MDA-MB231 ($2 \times 10^6$ cells/mouse) or B16F10 ($1 \times 10^6$ cells/mouse) cells were injected with into tail vein (8 mice/group). The development of lung metastases in mice with MDA-MB-231 was recorded using bioluminescence imaging at week 6. Mice with MDA-MB-231 cells were sacrificed at week 12 and visible lung metastatic nodules were examined macroscopically. Mice with B16F10 cells were sacrificed at day 12 and visible lung metastatic nodules were examined macroscopically. Data were analyzed using Student's t test. A P value less than 0.05 was considered significant.

Patient-Derived Xenograft Model

A patient-derived xenograft model was generated from an estrogen receptor-negative, progesterone receptor-negative, human epidermal growth factor receptor 2-negative ($ER^-PR^-\_HER2^-$) high-grade invasive ductal carcinoma. Briefly, freshly operated human breast tumor biopsy samples were implanted at the flank of immunodeficient mice NSG (NOD.Cg-Prkdcscid I12rgtm1Wj1/SzJ mice). When tumor size reached 1000 mm$^3$, mice were sacrificed, and tumor fragments (3 mm$^3$) were re-transplanted into mammary fat pads of additional mice. Passage 3 tumors were used to test the effect of PD0332991 on metastasis. When primary tumors reached 100-1.50 mm$^3$, mice were randomized and treated either with saline (n=8) or PD0332991 (100 mg/kg daily, PO n=8) for five weeks. Tumor volumes were measured once per week. After mice were sacrificed, and lung and liver metastatic nodules were examined macroscopically or detected in paraffin-embedded sections stained with ME. Data were analyzed using Student's t test. A P value less than 0.05 was considered significant.

Tissue Microarray

The tissue arrays of breast cancer samples were purchased from US Biomax (BR1101). Immunohistochemical staining of DUB3 (dilution 1:500) was carried out using IHC Select® HRP/DAB kit (Cat. DAB50, Millipore). The immunostaining was scored by pathologists of Mayo Clinic in a blinded manner. The score of tumor tissue was determined as compared to the staining intensity of normal tubules on the same slide. High and low polypeptide expression was defined using the mean score of all samples as a cutoff point. The chi-square test was used for statistical analysis of the correlation between DUB3 and SNAIL1, and the correlation of DUB3 or SNAIL1 with tissue type (non-metastatic carcinoma versus metastatic carcinoma).

chiStatistics

Data are expressed as mean±standard errors of the mean (SEM). Statistical analyses were performed with the Student's t-test or ANOVA. Statistical significance is represented in figures by: #, p<0.05; ##, p<0.01.

Denaturating Ni-NTA Pull-Down

Transiently transfected or virus infected cells were harvested, and pellets were washed once in PBS. Cells were lysed in 8M Urea, 0.1M NaH2PO4, 300 mM NaCl, and 0.01M Tris (pH 8.0). Lysates were briefly sonicated to shear DNA and incubated with Ni-NTA agarose beads (QIAGEN) for 1-2 hours at Room Temperature. Beads were washed 5 times with 8M Urea, 0.1M NaH2PO4, 300 mM NaCl, and 0.01M Tris (pH 8.0). Input and beads were boiled in loading buffer and subjected to SDS-PAGE and immunoblotting.

Denaturing Immunoprecipitation for Ubiquitination

The cells were lysed in 100 µL 62.5 mM Tris-HCl (PH 6.8), 2% SDS, 10% glycerol, 20 mM NEM, and 1 mM iodoacetamide, boiled for 15 min, diluted 10 times with NETN buffer containing protease inhibitors, 20 mM NEM, and 1 mM iodoacetamide, and centrifuged to remove cell debris. The cell extracts were subjected to immunoprecipitation with the indicated antibodies, and blotted as indicated.

In vitro Deubiquitinase Enzymatic Assay

In vitro enzymatic assays using ubiquitin-7-amido-4-methylcoumarin (Ub-AMC; U-550; Boston Biochem) were performed in 50-100 µL reaction buffer (20 mM HEPES-KOH [pH 7.8], 20 mM NaCl, 0.1 mg/mL ovalbumin [A7641; Sigma], 0.5 mM EDTA, and 10 mM DTT) at 25° C. Fluorescence was monitored in an Infinite® M1000 PRO Fluorometer (TECAN).

Migration and Invasion Assay

For migration assays (wound healing assays), cells were seeded in 6-well plates and grown until confluence, after which complete medium was replaced by serum-free medium, for 24 hours. Confluent cells (monolayer) was scraped with a P200 tip in each well, the medium was replaced with complete medium. After 24 hours, the cells were fixed with 3.7% Paraformaldehyde, and photographs were obtained. For matrigel invasion assays, cells were seeded in 24-well invasion chamber (Corning, 354480). Each sample was plated in triplicate. To measure of cell invasion, the filter was stained with 0.2% Crystal Violet, and invasion cells were counted.

Example 11—CDK1 Phosphorylates Ser41 of DUB3

Figure 15:
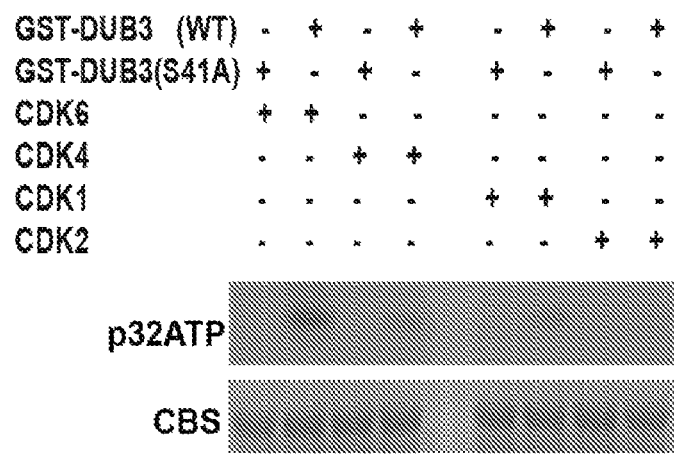
FIG. 15. CDK1 phosphorylates DUB3 at Ser41 in vitro, and the treatment of pan-CDK inhibitor Roscovitine decreased phosphorylation of DUB3. (A) Bacterially-expressed GST-DUB3 WT and GST-DUB3 S41A fusion polypeptides were incubated with active CDK4, CDK6, CDK1, or CDK2 in the presence of [γ-$^{32}$P]ATP. Polypeptides were resolved by SDS-PAGE, and phosphorylated polypeptides were visualized with autoradiography. CBS: Coomassie Blue Staining. (B) Cells were transfected with indicated plasmids, and were treated with vehicle, a pan-CDK inhibitor (Roscovitine), or a CDK4/6 inhibitor (PD0332991). Cell lysates were subjected to immunoprecipitation with an anti-FLAG antibody, and Western blotting was performed. Phosphorylation of Ser41 was examined.
Figure 15:
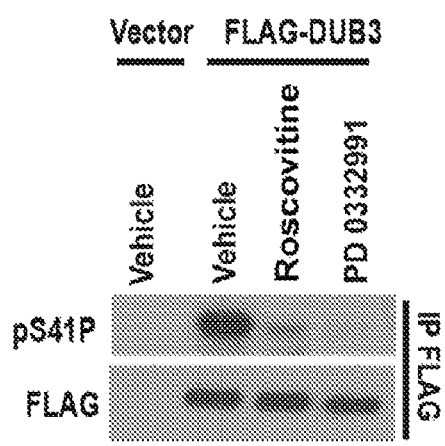
Figure 16:
FIG. 16. CDK1/2 inhibitor DU6027 decreases SNAIL1 polypeptide level in breast cancer cells. A Western blot of triple negative breast cancer cell (TNBC) line BT549 treated with CDK1/2 inhibitor (NU6027) for 18 hours at the indicated concentrations is shown.
Figure 17:
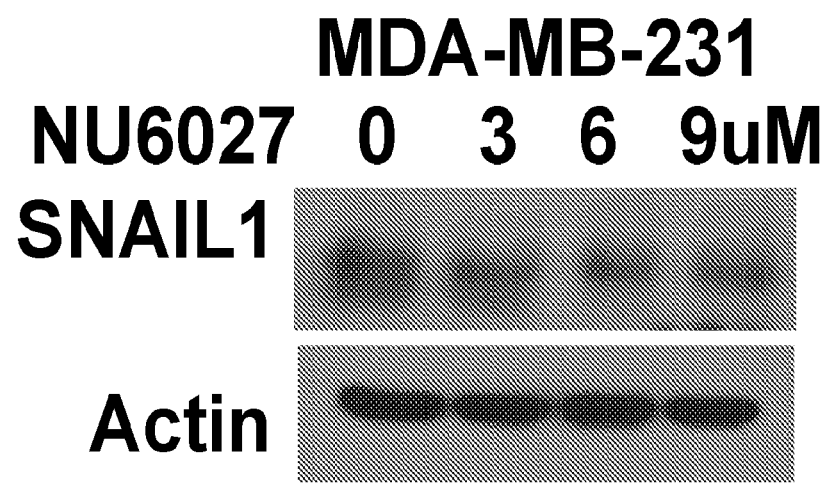
FIG. 17. CDK1/2 inhibitor DU6027 decreases SNAIL1 polypeptide level in breast cancer cells. A Western blot of triple negative breast cancer cell (TNBC) line MDA-MB-231 treated with CDK1/2 inhibitor (NU6027) for 18 hours at the indicated concentrations is shown.

It was tested whether other CDKs could directly phosphorylate DUB3. Bacterially-expressed GST-DUB3 WT and GST-DUB3 S41A fusion polypeptides were incubated with active CDK4, CDK6, CDK1 or CDK2 in the presence of [$\gamma$-$^{32}$P]ATP. As shown in FIG. 15A, CDK1 directly phosphorylated DUB3 in vitro. Cells were transfected with FLAG-DUB3 WT, and were treated with a pan CDK inhibitor (Roscovitine) or a selective inhibitor of CDK 4/6, PD0332991 (Palbociclib, Pfizer). CDK inhibition dramatically reduced the phosphorylation of DUB3 at Ser41 (FIG. 15B).

Example 12—CDK1/2 Inhibitor DU6027 Decreases SNAIL1 Polypeptide Level in Breast Cancer Cells Triple negative breast cancer cell (TNBC) line BT549 was treated with 0, 3, 6, or 9 µM of CDK1/2 inhibitor (NU6027) for 18 hours. Then cells were collected, and Western blotting was performed using SNAIL 1 or actin antibodies.

Example 13—CDK1/2 Inhibitor DU6027 Decreases SNAIL1 Polypeptide Level in Breast Cancer Cells Triple negative breast cancer cell (TNBC) line MDA-MB-231 was treated with 0, 3, 6, or 9 µM of CDK1/2 inhibitor (NU6027) for 18 hours. Then cells were collected, and Western blotting was performed using SNAIL 1 or actin antibodies.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer in a mammal, wherein said method comprises:
   (a) identifying said mammal as having cancer cells that express an elevated level of a DUB3 polypeptide or an elevated level of a SNAIL polypeptide, and
   (b) administering a CDK 4/6 inhibitor selected from the group consisting of PD0332991, LY2835219, and LEE011 to said mammal under conditions wherein said cancer cells do not metastasize.

2. The method of claim 1, wherein said mammal is a human.

3. The method of claim 1, wherein said cancer is a lung cancer, a breast cancer, or an ovarian cancer.

4. The method of claim 1, wherein said cancer is a triple negative breast cancer.

5. The method of claim 1, wherein said DUB3 polypeptide is phosphorylated at Ser41.

6. The method of claim 5, wherein said CDK 4/6 inhibitor inhibits phosphorylation of Ser41 of said DUB3 polypeptide.

* * * * *